(12) United States Patent
Scott

(10) Patent No.: US 8,252,840 B2
(45) Date of Patent: Aug. 28, 2012

(54) METHODS OF DERIVATIVES OF PROBUCOL FOR THE TREATMENT OF TYPE II DIABETES

(75) Inventor: Robert A. D. Scott, Roswell, GA (US)

(73) Assignee: Salutria Pharmaceuticals LLC, Alpharetta, GA (US)

( * ) Notice: Subject to any disclaimer, the term of this patent is extended or adjusted under 35 U.S.C. 154(b) by 609 days.

(21) Appl. No.: 12/055,926

(22) Filed: Mar. 26, 2008

(65) Prior Publication Data

US 2008/0280979 A1    Nov. 13, 2008

Related U.S. Application Data

(60) Provisional application No. 60/920,099, filed on Mar. 26, 2007.

(51) Int. Cl.
*A61K 31/19* (2006.01)
*A61K 31/235* (2006.01)

(52) U.S. Cl. .................. 514/571; 514/543; 514/866

(58) Field of Classification Search .................. 514/571, 514/543, 866
See application file for complete search history.

(56) References Cited

U.S. PATENT DOCUMENTS

| | | |
|---|---|---|
| 3,179,701 A | 4/1965 | Rocklin |
| 3,479,407 A | 11/1969 | Laufer |
| 3,576,883 A | 4/1971 | Neuworth |
| 3,952,064 A | 4/1976 | Whalley |
| 4,029,812 A | 6/1977 | Wagner |
| 4,076,841 A | 2/1978 | Wagner |
| 4,078,084 A | 3/1978 | Wagner |
| 4,115,590 A | 9/1978 | Lerner |
| 4,752,616 A | 6/1988 | Hall |
| 4,755,524 A | 7/1988 | Mueller et al. |
| 4,954,514 A | 9/1990 | Kita |
| 4,968,710 A | 11/1990 | Rustad |
| 4,975,467 A | 12/1990 | Ku et al. |
| 5,043,330 A | 8/1991 | Nguyen et al. |
| 5,061,734 A | 10/1991 | Mao et al. |
| 5,066,822 A | 11/1991 | Rustad et al. |
| 5,084,214 A | 1/1992 | Kita et al. |
| 5,112,870 A | 5/1992 | Mao et al. |
| 5,155,250 A | 10/1992 | Parker |
| 5,206,247 A | 4/1993 | Regnier |
| 5,262,439 A | 11/1993 | Parthasarathy |
| 5,278,014 A | 1/1994 | Tamaki |
| 5,294,724 A | 3/1994 | Jendralla et al. |
| 5,310,949 A | 5/1994 | Dufresne et al. |
| 5,380,747 A | 1/1995 | Medford |
| 5,411,741 A | 5/1995 | Zaias |
| 5,512,595 A | 4/1996 | Regnier et al. |
| 5,608,095 A | 3/1997 | Parker |
| 5,627,205 A | 5/1997 | Regnier et al. |
| 5,693,337 A | 12/1997 | Suzuki et al. |
| 5,739,374 A | 4/1998 | Janssen et al. |
| 5,750,351 A | 5/1998 | Medford |
| 5,773,209 A | 6/1998 | Medford et al. |
| 5,773,231 A | 6/1998 | Medford et al. |
| 5,783,596 A | 7/1998 | Medford et al. |
| 5,792,787 A | 8/1998 | Medford et al. |
| 5,807,884 A | 9/1998 | Medford et al. |
| 5,811,449 A | 9/1998 | Medford et al. |
| 5,821,260 A | 10/1998 | Medford et al. |
| 5,846,959 A | 12/1998 | Medford et al. |
| 6,037,377 A | 3/2000 | Anderskewitz et al. |
| 6,121,319 A | 9/2000 | Somers |
| 6,147,250 A | 11/2000 | Somers |
| 6,323,359 B1 | 11/2001 | Jass |
| 6,548,699 B1 | 4/2003 | Somers |
| 6,602,914 B2 | 8/2003 | Meng |
| 6,617,352 B2 | 9/2003 | Somers |
| 6,670,398 B2 * | 12/2003 | Edwards et al. ............. 514/571 |
| 6,828,447 B2 | 12/2004 | Meng et al. |
| 6,852,878 B2 * | 2/2005 | Meng et al. ..................... 562/42 |
| 7,187,870 B2 | 3/2007 | Ilchenko et al. |
| 7,375,252 B2 | 5/2008 | Meng et al. |
| 2002/0188118 A1 | 12/2002 | Meng |
| 2002/0193446 A1 | 12/2002 | Meng |
| 2003/0064967 A1 | 4/2003 | Luchoomun et al. |

FOREIGN PATENT DOCUMENTS

| | | |
|---|---|---|
| DE | 27 16 125 A1 | 10/1977 |
| EP | 0190682 | 8/1986 |
| EP | 0254272 A2 | 1/1988 |
| EP | 0292660 A2 | 11/1988 |
| EP | 0317165 B1 | 5/1989 |
| EP | 0348203 A1 | 12/1989 |
| EP | 0405788 A2 | 1/1991 |
| EP | 0418648 A1 | 3/1991 |
| EP | 0621255 A1 | 10/1994 |
| EP | 0763527 A1 | 3/1997 |
| EP | 0866049 A2 | 9/1998 |
| FR | 2130975 A5 | 11/1972 |
| FR | 2133024 A5 | 11/1972 |
| FR | 2134810 A5 | 12/1972 |

(Continued)

OTHER PUBLICATIONS

Gorogawa et al., "Probucol preserves pancreatic β-cell function through reduction oxidative stress in type 2 diabetes", Diabetes Research and Clinical Practice, vol. 57, No. 1, pp. 1-10 (2002).*

Anonymous, "AtheroGenics announces positive Phase II results from CART-1 Clinical Trial for restenosis," (Press Release Nov. 12, 2001).

Anonymous, "AtheroGenics: Faster than anticipated," *BioCentury Extra* (*The Bernstein Report of Biobusiness*), Reprint from May 29, 2001.

Barnhart, J.W., et al., Chapter 10: The Synthesis, metabolism, and biological activity of probucol and its analogs, *Pharmacochem. Libr.*, 1991(17):277-299 (1991). XP002095165.

(Continued)

*Primary Examiner* — Kevin E Weddington
(74) *Attorney, Agent, or Firm* — King & Spalding

(57) ABSTRACT

This present invention provides methods and pharmaceutical compositions for the treatment or prophylaxis of diabetes and related disorders, comprising the administration of an effective amount of a monoester of probucol, particularly the monosuccinic acid ester, or a pharmaceutically acceptable salt or derivative thereof.

27 Claims, 20 Drawing Sheets

FOREIGN PATENT DOCUMENTS

| | | |
|---|---|---|
| FR | 2140769 A5 | 1/1973 |
| FR | 2140771 A5 | 1/1973 |
| FR | 2168137 A1 | 8/1973 |
| GB | 1136539 | 12/1968 |
| GB | 1148550 | 4/1969 |
| GB | 1199871 A | 7/1970 |
| JP | 49-075552 A | 7/1974 |
| JP | 06-312978 A | 11/1994 |
| JP | 73-28425 | 12/1995 |
| JP | 09-059258 A | 3/1997 |
| WO | WO 93/02051 A2 | 2/1993 |
| WO | WO 94/07869 A1 | 4/1994 |
| WO | WO 95/09158 A1 | 4/1995 |
| WO | WO 95/15760 A1 | 6/1995 |
| WO | WO 95/17408 A1 | 6/1995 |
| WO | WO 95/30415 A1 | 11/1995 |
| WO | WO 96/12703 A1 | 5/1996 |
| WO | WO 96/20197 A1 | 7/1996 |
| WO | WO 97/15546 A1 | 5/1997 |
| WO | WO 97/26258 A1 | 7/1997 |
| WO | WO 97/48694 A1 | 12/1997 |
| WO | WO 98/22418 A1 | 5/1998 |
| WO | WO 98/51289 A2 | 11/1998 |
| WO | WO 98/51662 A2 | 11/1998 |
| WO | WO 99/15159 A2 | 4/1999 |
| WO | WO 99/24400 A1 | 5/1999 |
| WO | WO 00/26167 A1 | 5/2000 |
| WO | WO 00/26184 A1 | 5/2000 |
| WO | WO 00/28332 A1 | 5/2000 |
| WO | WO 00/31053 A1 | 6/2000 |
| WO | WO 00/59509 A1 | 10/2000 |
| WO | WO 01/70757 A2 | 9/2001 |
| WO | WO 01/70757 A3 | 9/2001 |
| WO | WO 01/79164 A2 | 10/2001 |
| WO | WO 01/79164 A3 | 10/2001 |
| WO | WO 03/028241 A | 5/2003 |
| WO | WO 03/039231 | 5/2003 |
| WO | WO 03/039352 | 5/2003 |
| WO | WO 2005/112914 | 12/2005 |
| WO | WO 2006/007508 | 1/2006 |
| WO | WO 2008/140781 A | 11/2008 |

OTHER PUBLICATIONS

Baron, J.L., et al., "The pathogenesis of adoptive murine autoimmune diabetes requires an interaction between α-4-integrins and vascular cell adhesion molecule-1", *J. Clin. Invest.* 93:1700-1708 (Apr. 1994).
Brown, et al., "Lipoprotein metabolism in the macrophage: implications for cholesterol deposition in atherosclerosis", *Ann. Rev. Biochem.*, 52:223-261 (1983).
Burkly, L.C., et al., "Protection against adoptive transfer of autoimmune diabletes mediated through very late antigen-4 integrin", *Diabetes*, 43:529-534 (Apr. 1994).
Carew, et al., "Antiatherogenic effect of probucol unrelated to its hypocholesterolemic effect: Evidence that antioxidants in vivo can selectively inhibit low density lipoprotein degradation in macrophage-rich fatty streaks and slow the progression of atherosclerosis in the Watanabe heritable hyperlipidemic rabbit", *Proc. Natl. Acad. Sci. U.S.A.*, 84:7725-7729 (Nov. 1987).
Cominacini, L., et al., *Free Radical Biology and Medicine*, 22(1/2):117-127 (1996) XP002095164.
De Meglio, P., "New derivatives of clofibrate and probucol. Preliminary studies on hypolipemic activity," *Il Farmaco, Ed. Sci.* 40(11):833-844 (1985). With partial translation. *Chem. Abstracts*, 104(5):28675, (Feb. 3, 1986), XP 002124424.
Feldman, D., et al., "The In Vitro and Ex Vivo Antioxidant Properties, and Hypolipidemic Activity of CGP 2881," *Atherosclerosis*, 144:343-355 (Dec. 28, 1998).
Folkman, J., et al., "Angiogenesis", *J. Biol. Chem.*, 267(16):10931-10934 (Jun. 5, 1992).
Fruebis, J., "A Comparison of the Antiatherogenic Effects of Probucol and of a Structural Analogue of Probucol in Low Density Lipoprotein Receptor-deficient Rabbits," *The American Society for Clincial Investigation, Inc.*, 94:392-398 (Jul. 1994).
Gershbein et al., "Action of drugs and chemical agents on rat liver regeneration," *Drug and Chemical Toxicology*, 8(3):125-143 (1985).
Heeg, et al., "Plasma levels of Probucol in man after single and repeated oral doses", *La Nouvelle Presse Medicale*, 9(40):2990-2994 (Oct. 30, 1980). Abstract in English.
Iademarco, M.F., et al., "Characterization of the promoter for vascular cell adhesion molecule-1 (VCAM-1)", *J. Biol. Chem.* 267(23):16323-16329 (Aug. 15, 1992).
Kelarev, V.I., et al., *Khim. Geterotsikl. Soedin*, No. 5, pp. 667-673 (1995). Provided as *Chem. Abstracts*, AN 124:146082, XP002115604.
Kelarev, V.I., et al., *Khim. Geterotsikl. Soedin.*, No. 4, pp. 514-517 (1995). Provided as *Chem. Abstracts* AN 124(1):8690 (Jan. 1, 1996) XP002115603 and XP002115596.
Koch, A.E., et al., "Immunolocalization of endothelial and leukocyte adhesion molecules in human rheumatoid and osteoarthritic synovial tissues", *Lab. Invest.*, 64(3):313-320 (1991).
Lankin, V.Z., et al., *Dokl. Akad. Nauk.*, 351(4):554-557 (1996), *Chem. Abstracts*, AN 127(6):75973u (1997), XP002115597.
Mamedov, Ch.I., et al., *Mater. Nauchn. Konf. Aspir. Akad. Nauk Az. SSR*, 1:127-131 (1980), *Chem. Abstracts*, AN 94:30290c (1981), XP002115600.
Mao., S.J., et al., "Antioxidant Activity of Probucol and Its Analogues in Hypercholesterolemic watanabe Rabbits," *Journal of Medicinal Chemistry*, 34(1):298-302 (Jan. 1991).
Mao, S.J., et al., "Attenuation of Atherosclerosis in a Modified Strain of Hypercholesterolemic Watanabe Rabbits with Use of a Probucol Analogue (MDL29,311) That Does Not Lower serum Cholesterol," *Arteriosclerosis and Thrombosis*,11(5):1266-1275 (Sep.-Oct. 1991).
Medvedev, A.I., et al., *Tezisy Dokl. Nauchn. Sess. Khim. Tekhnol. Org. Soedin. Sery Sernistykh Neftei, 13th*, pp. 123-124 (1974), *Chem. Abstracts*, AN 86(1):5066m (p. 437, Jan. 3, 1977). XP002115601, XP00215594.
Miller, G.J., "High density lipoproteins and atherosclerosis", *Ann. Rev. Med.*, 31:97-108 (1980).
Morales-Ducret, J., et al., "α4/β1 integrin (VLA-4) ligands in arthritis: vascular cell adhesion molecule-1 expression in synovium and on fibroblast-like synoviocytes", *J. Immunol.*, 149(4):1424-1431 (Aug. 15, 1992).
Neuworth, M.B., "Synthesis and hypocholesterolemic activity of alkylidenedithio bisphenols," *J. Med. Chem.*, 13(4) 722-725 (1970), *Chem. Abstracts* AN 73:445047 (1970), XP002124423.
Ohkawara, Y., et al., "In situ expression of the cell adhesion molecules in bronchial tissues from asthmatics with air flow limitation: In vivo evidence of VCAM-1/VLA-4 interaction in selective eosinophil infiltration", *Am. J. Respir. Cell. Mol. Biol.*, 12:4-12 (1995).
Orosz, C.G., et al., "Role of the endothelial adhesion molecule VCAM in murine cardiac allograft rejection", *Immunol. Lett.*, 32:7-12 (1992).
Parthasarathy, S., et al., "Probucol inhibits oxidative modification of low density lipoprotein", *J. Clin. Invest.*, 77 :641-644 (1986).
Pastor, S.D., et al., *Phosphorus and Sulfur*, 37(3-4):117-123 (1988), *Chemical Abstracts*, AN 110(23):212254a (Jun. 5, 1989), XP0021156682.
Pilewski, J.M., et at, "Cell adhesion molecules in asthma: homing, activation, and airway remodeling", *J. Respir. Cell. Mol. Biol.*, 12:1-3 (1995).
Rabb, H.A., et al., "The role of the leukocyte adhesion molecules VLA-4, LFA-1 and Mac-1 in allergic airway responses in the rat", *Am. J. Respir. Crit. Care Med.*, 149:1186-1191 (1994).
Ramasamy, S., et al., "Modulation of Expression of Endothelial Nitric Oxide Synthase by Nordihydroguaiaretic Acid, a Phenolic Antioxidant in Cultured Endothelial Cells," *Molecular Pharmacology*, 56(1):116-123 (Apr. 5, 1999).
Rinninger, et al. , "Probucol enhances selective uptake of HDL-associated cholesteryl esters in vitro by a scavenger receptor B-I-dependent mechanism", *Atherioschler. Throm. Vasc. Biol.*, 19:1325-1332 (1999). XP-008001008.
Roberts, C.P., et al., "Regulation of Monocyte Macrophage Differentiation by Antiglucocorticods and Antioxidants, " *American Journal of Obstetrics and Gynecology*, 179(2): 354-62 (Aug. 1998).
Sawayama, Y., et al., "Effects of Probucol and Pravastatin on common carotid atherosclerosis in patients with asymptomatic hypercholesterolemia", *Journal of the American College of Cardiology*, 39(4):610-616 (2002).

Steinberg, D., et al., "Modifications of low-density lipoprotein that increase its atherogenicity", *N. Eng. J. Med.*, 220(14):915-924 (1989).

Tomich et al., *Chemical Abstracts*, AN 127(6):75971s (1997).

Wagner, Jr., et al., *Chemical Abstracts*, AN 82:86189w (1975).

Yang, X.-D., et al., "Inhibition of insulitis and prevention of diabetes in nonobese diabetic mice by blocking L-selectin and very late antigen 4 adhesion receptors", *Proc. Natl. Acad. Sci. U.S.A.*, 90:10494-10498 (1993).

Kajimoto, Y., "Agent for Treating and Preventing Diabetes Mellitus contains, Probucol, its salt or Solvent as Active Ingredient," *WPI/Thomson abstract*, vol. 2002, No. 69, May 9, 2002.

Gorogawa, Shin-Ichi et al., "Probucol Preserves Pancreatic Beta-Cell Function through Reduction of Oxidative Stress in Type 2 Diabetes," *Diabetes Research and Clinical Practice*, vol. 57, No. 1, Jul. 1, 2002.

Meng, C. Q. et al., "Novel Phenolic Antioxidents as Multifunctional Inhibitors of Inducible VCAM-1 Expression for Use in Atherosclerosis," *Bioorganic & Medicinal Chemistry Letters Pergamon*, Elsevier Science, vol. 12, No. 18, Jan. 16, 2002.

Sundell, Cynthia L. et al., "AGI-1067: a multifunctional phenolic antioxidant, lipid modulator, anti-inflammatory and antiatherosclerotic," Jour. Pharm and Experiment. Therapeutics, vol. 305, pp. 1116-1123, Jun. 2003.

\* cited by examiner

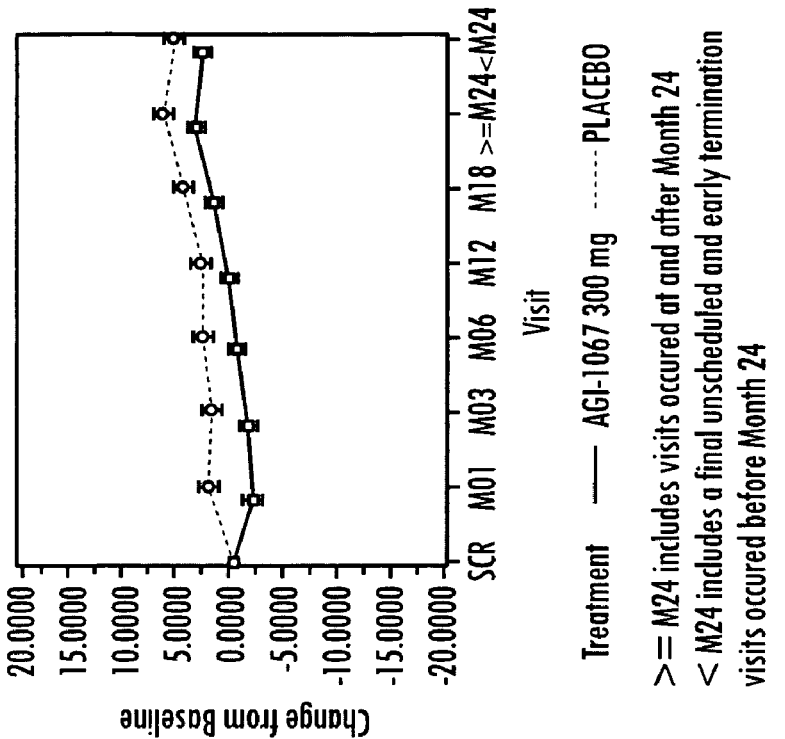
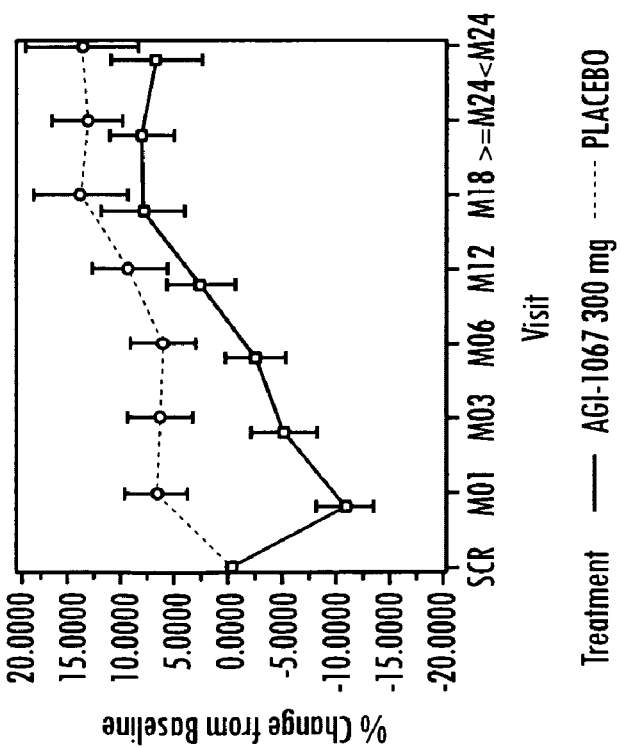
CHANGE FROM BL IN GLUCOSE - DIABETICS AND NON DIABETICS
Fig. 2

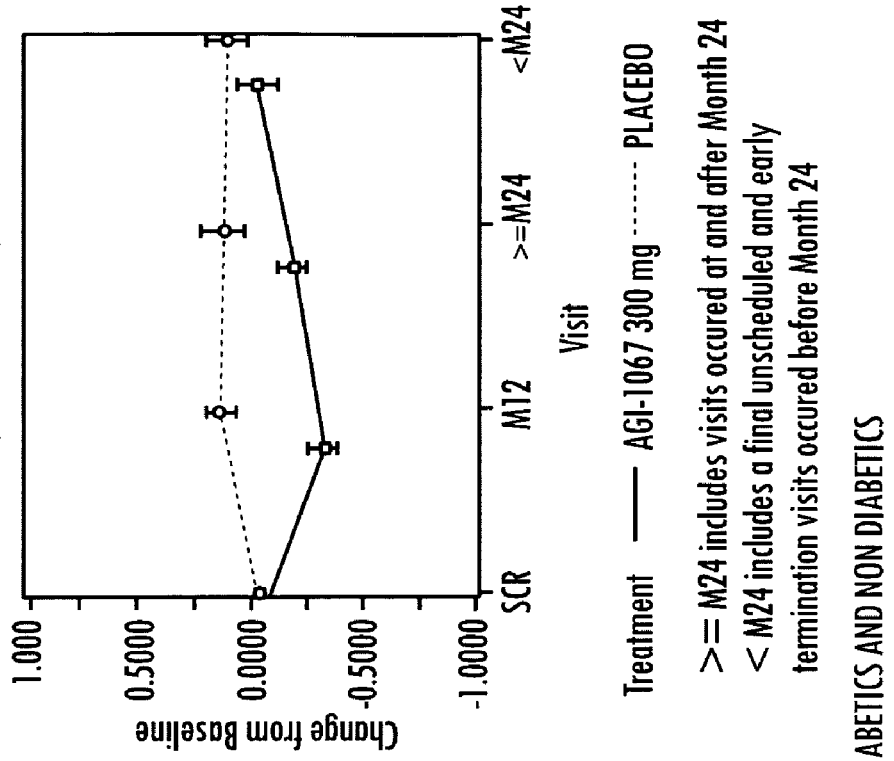
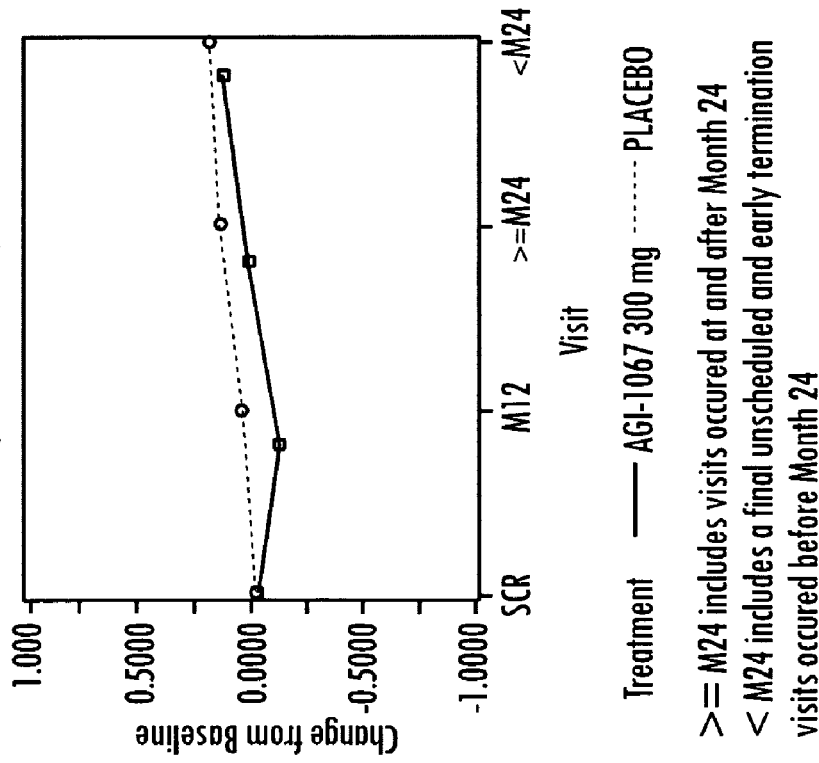
Fig. 3
CHANGE FROM BL IN GLUCOSE - DIABETICS AND NON DIABETICS

FIGURE 7: CHANGE IN HBA1C FOR SUBJECTS ON PIOGLITAZONE AT BASELINE

FIGURE 13: EGFR - PERCENT CHANGE FROM BASELINE

FIGURE 15: ADVERSE EVENTS POSSIBLY RELATED TO DIABETIC CONTROL

|  | Placebo (n=3038) | AGI-1067 (n=3049) |
|---|---|---|
| Blood glucose increased | 108 | 64 |
| DM aggravated | 79 | 81 |
| DM inadequate control | 43 | 31 |
| Hyperglycemia NOS | 35 | 25 |
| Glycosylated hemoglobin increased | 33 | 18 |
| Diabetes mellitus NOS | 14 | 9 |
| Blood glucose fluctuations | 15 | 5 |
| Blood glucose abnormal | 9 | 4 |
| Glucose urine present | 11 | 1 |
| Glucose tolerance impaired | 4 | 2 |
| Blood glucose decreased | 1 | 5 |
| Glycosuria | 2 | 0 |

ABSOLUTE CHANGE IN EGFR (ESTIMATED GLOMERULAR FILTRATION RATE)

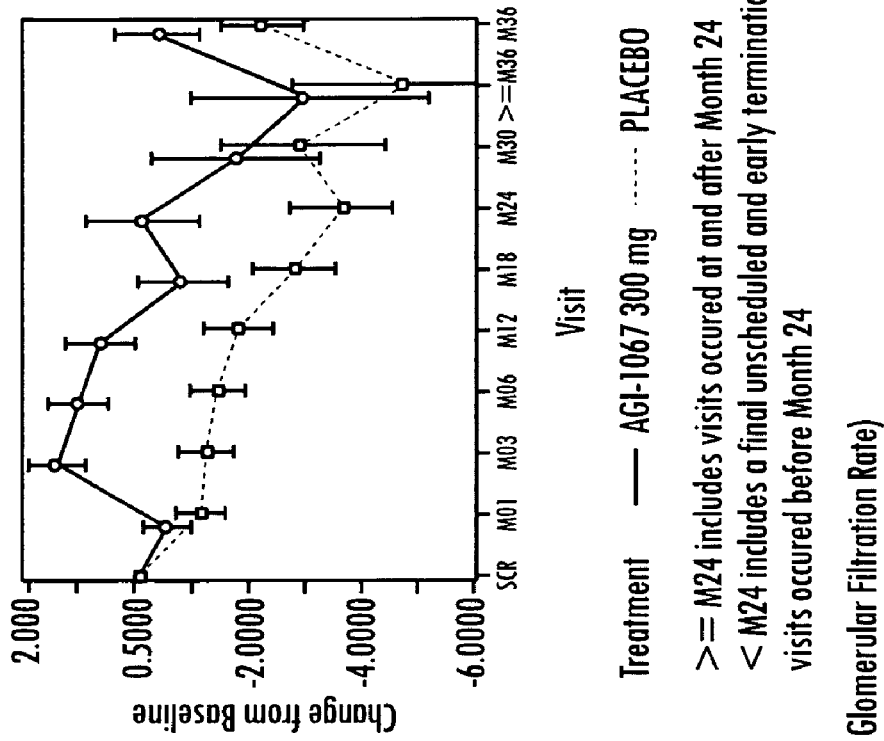
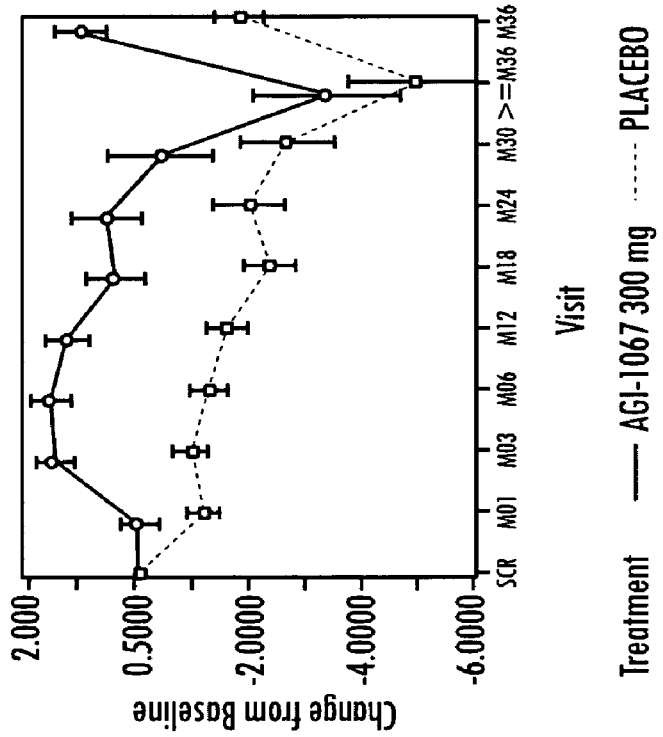
Fig. 17

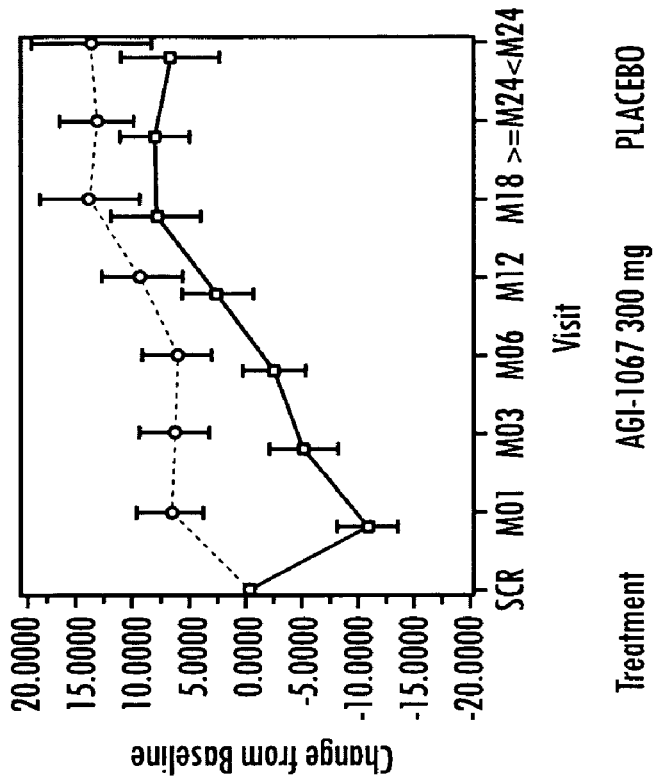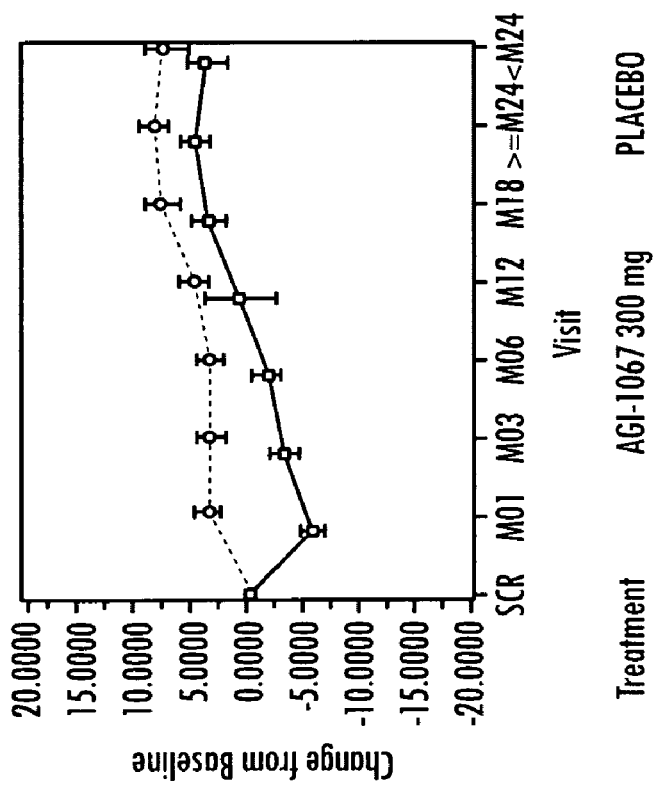
Fig. 20
CHANGE FROM BL IN GLUCOSE - DIABETICS AND IMPAIRED FASTING GLUCOSE

METHODS OF DERIVATIVES OF PROBUCOL FOR THE TREATMENT OF TYPE II DIABETES

CROSS-REFERENCE TO RELATED APPLICATIONS

This application claims priority to U.S. Provisional Application 60/920,099, filed Mar. 26, 2007.

FIELD OF THE INVENTION

This present invention provides methods and pharmaceutical compositions for the treatment or prophylaxis of diabetes and related disorders, comprising the administration of an effective amount of a monoester of probucol, particularly the monosuccinic acid ester, or a pharmaceutically acceptable salt or derivative thereof.

BACKGROUND OF THE INVENTION

Diabetes, also referred to as diabetes mellitus, is a syndrome characterized by hyperglycemia resulting from absolute or relative impairment in insulin secretion and/or insulin action (The Merck Manual of Diagnosis and Therapy, 17$^{th}$ Ed, Section 2, Chapter 13; Berkow, R., Beers, M. H., and Burs, M., Eds.; John Wiley & Sons, 1999). It is characterized as a progressive breakdown in normal insulin-related usage of glucose. In order to function properly, the body's use of glucose must comprise a balanced output of insulin from the pancreas to transport glucose effectively to other organs and tissues for storage. Any insulin imbalance or loss of sensitivity can cause a chronic overabundance of glucose leading to diabetes.

In 2006, according to the World Health Organization, at least 171 million people worldwide suffer from diabetes. Its incidence is increasing rapidly, and it is estimated that by the year 2030, this number will double. Diabetes mellitus occurs throughout the world, but is more common (especially type 2) in the more developed countries.

For at least 20 years, diabetes rates in North America have been increasing substantially. According to the American Diabetes Association, it is estimated that a total of 20.8 million people in the United States, about 7.0% of the population, have diabetes in one form or another, and of these people, about 6.2 million people undiagnosed. (http://www.diabetes.org/diabetes-statistics/prevalence.jsp). Additionally, about 54 million people are predicted to be presently prediabetic.

Fasting Plasma Glucose Test (FPG) or an Oral Glucose Tolerance Test (OGTT) are used to diagnose pre-diabetes or diabetes. With the FPG test, a fasting blood glucose level between 100 and 125 mg/dl signals pre-diabetes. A fasting blood glucose level of 126 mg/dl or higher indicates diabetes. In the OGTT test, a person's blood glucose level is measured after a fast and two hours after drinking a glucose-rich beverage. If the two-hour blood glucose level is between 140 and 199 mg/dl, the person tested has pre-diabetes. If the two-hour blood glucose level is at 200 mg/dl or higher, the person tested has diabetes.

There are several types of diabetes. In type 1 diabetes, (also called insulin-dependent diabetes mellitus (IDDM) or juvenile-onset diabetes or autoimmune diabetes) patients produce little or no insulin, the hormone which regulates glucose utilization, because the immune system attacks the cells in the pancreas that make and release insulin. As these cells die, blood sugar levels rise. Generally, type I diabetes is characterized clinically by hyperglycemia and a propensity to develop diabetic ketoacidosis (DKA), wherein the pancreas produces little or no insulin. Thus, people with type 1 diabetes need insulin shots. Type 1 diabetes, which accounts for 5% to 10% of all diagnosed cases of diabetes, typically affects children, although adults can develop it. Autoimmune, genetic, and environmental factors are involved in the development of this type of diabetes.

Type 2 diabetes, or noninsulin-dependent diabetes mellitus (NIDDM) or adult-onset diabetes, usually develops later in life. Insulin is still produced in the body, however the organs and tissues lose their ability to respond effectively to insulin. Although type 2 diabetes is also characterized by hyperglycemia and insulin resistance, it is often associated with visceral/abdominal obesity, has very little or no propensity to ketoacidosis. It is typically diagnosed in patients older than 30, and has significant but variable levels of insulin secretion relative to plasma glucose levels. The CDC estimates type 2 diabetes may account for about 90% to 95% of all diagnosed cases of diabetes. Risk factors for type 2 diabetes include older age, obesity, family history of diabetes, prior history of gestational diabetes, impaired glucose tolerance, physical inactivity, and race/ethnicity. African Americans, Hispanic/Latino Americans, American Indians, and some Asian Americans and Pacific Islanders are at particularly high risk for type 2 diabetes.

Gestational diabetes is a third type of diabetes that develops in about 4% percent of all pregnancies—about 135,000 cases in the United States each year—and usually ends with the pregnancy. A small percentage of diabetes may also result from specific genetic syndromes, surgery, drugs, malnutrition, infections, and other illnesses.

Additionally, millions of people have a condition called pre-diabetes. They have higher-than-normal blood sugar levels, but not high enough to be clinically defined as diabetics. These people are at extremely high risk for developing type 2 diabetes. It has been suggested that both impaired fasting glucose (IFG) and impaired glucose tolerance (IGT) are intermediate states in the transition from normal glucose tolerance (NGT) to type 2 diabetes and have been termed as "pre-diabetes". They are associated with a high risk for progression to type 2 diabetes. Hepatic glucose production (HGP) is the principal determinant of fasting plasma glucose (FPG). It has been demonstrated that, in the non-diabetic range, the rise in fasting plasma glucose (FPG) concentration is associated with a mild decrease in hepatic glucose production (HGP) and a marked decrease in the glucose clearance rate. During the fasting state, the decrease in glucose clearance results in an increase in FPG concentration which stimulates basal insulin secretion. The rise in fasting plasma insulin concentration, in turn, inhibits HGP, thus attenuating the rise in FPG. The high fasting blood glucose in these subjects can thus be explained by the decrease in glucose clearance. (Rucha Jani, abstract of American Association of Clinical Endocrinologists Sixteenth Annual Meeting and Clinical Congress, Apr. 11-16, 2007, Washington State Convention & Trade Center in Seattle).

The chronic overabundance of glucose associated with diabetes damages the body's blood vessels and can lead to many related disorders. Generally, high glucose levels in the blood plasma (hyperglycemia) can lead higher than normal amounts of particular hemoglobin, HbA1c. Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease.

Patients with type 2 diabetes mellitus have a significantly increased risk of macrovascular and microvascular complications. In extreme cases, diabetes can result in the amputation of limbs and death.

Diabetes is also the leading cause of kidney failure in the U.S. (see American Kidney Fund, 2007; Middleton, et al. (2006) The unrecognized prevalence of chronic kidney disease in diabetes. *Nephrology Dialysis Transplantation* 21 (1):88-92). In fact, almost 45% of all kidney failure cases are caused by diabetes. Drugs and diet can help manage diabetes and prevent complications, but some people may still develop kidney disease, even with good medical care.

Other conditions related to diabetes reported by the CDC include: nervous system diseases, which often includes impaired sensation or pain in the feet or hands, slowed digestion of food in the stomach, carpal tunnel syndrome, and other nerve problems, periodontal disease, which is a type of gum disease that can lead to tooth loss, complications of pregnancy, including congenital malformations and death of the fetus, and other complications such as diabetic ketoacidosis and hyperosmolar nonketotic coma. Many patients who have insulin resistance or type 2 diabetes also often have several symptoms that together are referred to as syndrome X, or the metabolic syndrome.

Current Therapies for Diabetes

Therapeutic control of glucose homeostasis, lipid metabolism, obesity, and hypertension have been considered critically important in the clinical management and treatment of diabetes mellitus. Lack of insulin production by the pancreas makes type 1 diabetes particularly difficult to control. Treatment generally requires a strict lifestyle regimen including multiple daily insulin injections.

Current drugs used for managing type 2 diabetes, generally fall within five classes of compounds: the biguanides, thiazolidinediones, the sulfonylureas, benzoic acid derivatives and alpha-glucosidase inhibitors. The biguanides, such as metformin, are believed to prevent excessive hepatic gluconeogenesis. The thiazolidinediones are believed to act by increasing the rate of peripheral glucose disposal. The sulfonylureas, such as tolbutamide and glyburide, the benzoic acid derivatives, such as repaglinide, and the alpha-glucosidase inhibitors, such as acarbose, lower plasma glucose primarily by stimulating insulin secretion.

A widely used drug treatment involves the administration of meglitinide or a sulfonylurea (e.g. tolbutamide or glipizide), which are insulin secretagogues. These drugs increase the plasma level of insulin by stimulating the pancreatic β-cells to secrete more insulin. Dangerously low levels of plasma glucose can result from administration of insulin and/or insulin secretagogues, and an increased level of insulin resistance can occur.

The biguanides are another class of drugs that are widely used to treat type 2 diabetes. The two best known biguanides, phenformin and metformin, cause some correction of hyperglycemia without risk of causing hypoglycemia. However, phenformin and metformin can induce lactic acidosis and nausea/diarrhea.

The glitazones (i.e. 5-benzylthiazolidine-2,4-diones) can ameliorate hyperglycemia and other symptoms of type 2 diabetes. These agents substantially increase insulin sensitivity in muscle, liver and adipose tissue in several animal models of type 2 diabetes, resulting in partial or complete correction of elevated plasma glucose levels without the occurrence of hypoglycemia. The glitazones that are currently marketed (rosiglitazone and pioglitazone) are agonists of the peroxisome proliferator activated receptor (PPAR) gamma subtype. PPAR-gamma agonism is generally believed to be responsible for the improved insulin sensititization that is observed with the glitazones.

Probucol Derivatives

Derivatives of probucol have been developed as therapeutics, for example, for the treatment of cardiovascular disease and as anti-inflammatory agents. Probucol contains two hydroxyl groups and can be modified to form mono-substituted or di-substituted derivatives. Mono-esters and ethers of probucol have been reported to be useful in the treatment of inflammatory diseases such as rheumatoid arthritis, osteoarthritis, asthma, and dermatitis. Methods for treating transplant rejection using mono-substituted derivatives of probucol also have been reported. See U.S. Pat. Nos. 6,670,398 and 7,087,645.

U.S. Pat. No. 5,262,439 to Parthasarathy discloses analogs of probucol with increased water solubility in which one or both of the hydroxyl groups are replaced with ester groups that increase the water solubility of the compound. A series of French patents disclose that certain probucol derivatives are hypocholesterolemic and hypolipemic agents: FR 2168137 (bis 4hydroxyphenylthioalkane esters); FR 2140771 (tetralinyl phenoxy alkanoic esters of probucol); FR 2140769 (benzofuryloxyalkanoic acid derivatives of probucol); FR 2134810 (bis-(3-alkyl-5-t-alkyl-4-thiazole-5-carboxy)phenylthio)alkanes; FR 2133024 (bis-(4 nicotinoyloxyphenylthio)-propanes; and FR 2130975 (bis(4-phenoxyalkanoyloxy)phenylthio)alkanes).

European Patent No. 0348203 to Shiongi Seiyaku Kabushiki Kaisha discloses phenolic thioethers which inhibit the denaturation of LDL and the incorporation of LDL by macrophages. Hydroxamic acid derivatives of these compounds are disclosed in European Patent No. 0405788 to Shiongi Seiyaku Kabushiki Kaisha and are alleged as useful for the treatment of arteriosclerosis, ulcer, inflammation and allergies. Carbamoyl and cyano derivatives of the phenolic thioethers are disclosed in U.S. Pat. No. 4,954,514 to Kita, et al.

WO 98/51662 (also U.S. Pat. No. 6,121,319) and WO 98/51289 (also U.S. Pat. No. 6,147,250) to AtheroGenics, Inc. describe certain probucol derivatives and their use for the treatment of disorders mediated including inflammatory and cardiovascular disorders.

WO 01/70757 (also U.S. Pat. No. 6,852,878) to AtheroGenics, Inc. also describes the use of certain thioethers of the following formula, and pharmaceutically acceptable salts thereof:

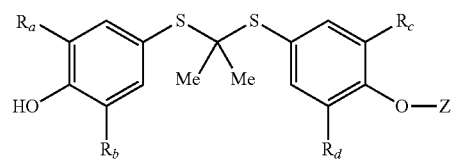

wherein
$R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and Z is (i) a substituted or unsubstituted carbohydrate, (ii) a substituted or unsubstituted alditol, (iii) $C_{1-10}$ alkyl or substituted $C_{1-10}$ alkyl, terminated by sulfonic acid, (iv) $C_{1-10}$ alkyl or substituted $C_{1-10}$ alkyl, terminated by phosphonic acid, (v) substituted or unsubstituted $C_{1-10}$ alkyl-O—C(O)—$C_{1-10}$ alkyl; (vi) straight chained polyhydroxylated $C_{3-10}$ alkyl; (vii) —$(CR_2)_{1-6}$—COOH, wherein R is independently hydrogen, halo, amino, or hydroxy, and wherein at least one of the R substituents is not hydrogen; or (viii) —$(CR_2)_{1-6}$—X, wherein X is aryl, heteroaryl, or heterocycle, and R is independently hydrogen, halo, amino, or hydroxy.

Meng et al., discloses a series of phenolic inhibitors of TNF-inducible expression of VCAM-1 with concurrent antioxidant and lipid-modulating properties. The compounds disclosed have demonstrated efficacies in animal models of atherosclerosis and hyperlipidemia. (Novel Phenolic Antioxidants as Multifunctional Inhibitors of Inducible VCAM-1 Expression for Use in Atherosclerosis, *Bioorganic & Med. Chem Ltrs.* 12 (18), 2545-2548, 2002).

WO2006/007508 to AtheroGenics, Inc. (also U.S. Patent Publication No. 20060058268) describes methods for treating certain microvascular diseases related to diabetes, including neuropathy, nephropathy, or retinopathy in a mammal, the method comprising administering to the mammal an effective amount of certain probucol derivatives Given the high and increasing incidence of diabetes worldwide, there is a need to provide new therapies for its treatment.

Therefore, it is an object of the present invention to provide pharmaceutical compositions and methods for treatment or prophylaxis of diabetes and related disorders.

SUMMARY

In one embodiment, the invention provides a method for the treatment or prophylaxis of diabetes, a pre-diabetes condition or a diabetes related disorder in a host, comprising administering a compound of formula (A), or a pharmaceutically acceptable salt, ester, pharmaceutically acceptable derivative, or prodrug thereof:

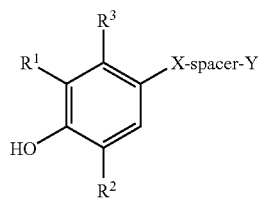

(A)

wherein

X, Y, spacer, $R^1$, $R^2$, $R^3$ and $R^4$ are defined herein.

In a further embodiment, a method for the treatment or prophylaxis of diabetes, a pre-diabetes condition or a diabetes related disorder in a host, comprising administering a compound of formula (B), or a pharmaceutically acceptable salt, ester, pharmaceutically acceptable derivative, or prodrug thereof, is provided:

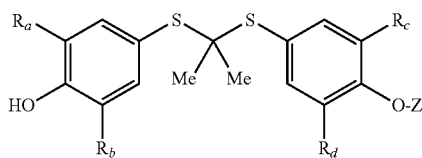

(B)

wherein Z, $R_a$, $R_b$, $R_c$, and $R_d$ are defined herein.

In one more particular embodiment, the invention provides a method for the treatment or prophylaxis of diabetes, a pre-diabetes condition or a diabetes related disorder in a host, comprising administering a compound of Formula I:

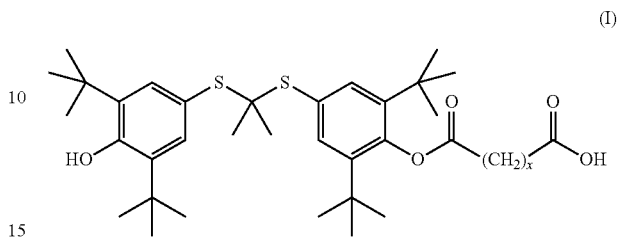

(I)

wherein x is selected from 1, 2, 3 or 4;
or a pharmaceutically acceptable salt, ester, pharmaceutically acceptable derivative, or prodrug thereof.

In a specific subembodiment, the compound is a monosuccinic acid ester of probucol of the structure:

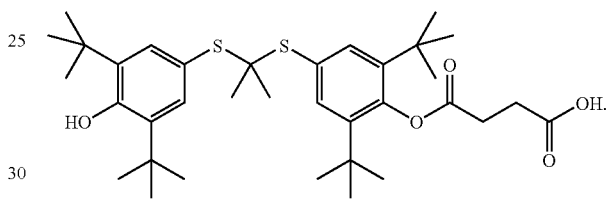

In another more particular embodiment, the invention provides a method for the treatment or prophylaxis of diabetes, a pre-diabetes condition or a diabetes related disorder in a host, comprising administering a compound of Formula II:

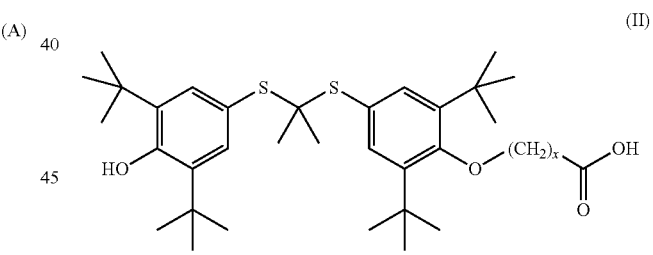

(II)

wherein x is selected from 1, 2, 3 or 4;
or a pharmaceutically acceptable salt, ester, pharmaceutically acceptable derivative, or prodrug thereof. In a specific embodiment, x is 1. In another embodiment, x is 2. In another embodiment, x is 3. In another embodiment, x is 4.

In one embodiment, the compound is of the structure:

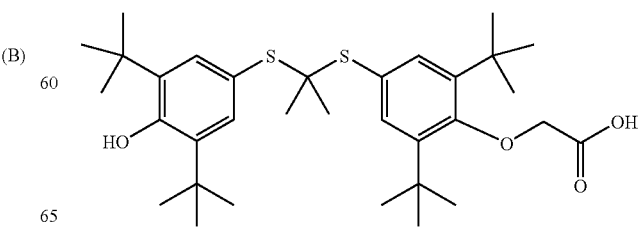

In one embodiment, a method of prophylaxis of a host at risk of developing diabetes is provided, including administering an effective amount of a compound of Formula A, B, I or II, a monosuccinic acid ester of probucol, or a pharmaceutically acceptable salt, ester, pharmaceutically acceptable derivative, or prodrug thereof.

In one embodiment, a method of treatment of a host who has been diagnosed with diabetes is provided, including administering an effective amount of a compound of Formula A, B, I or II, or a monosuccinic acid ester of probucol, or a pharmaceutically acceptable salt, ester, pharmaceutically acceptable derivative, or prodrug thereof.

In one embodiment, the host at risk of or diagnosed with diabetes is at risk of or diagnosed with type 2 diabetes.

In one embodiment, a method of glycemic control in a host in need thereof is provided, including administering an effective amount of a compound of Formula A, B, I or II, or a monosuccinic acid ester of probucol, or a pharmaceutically acceptable salt, ester, pharmaceutically acceptable derivative, or prodrug thereof.

In one embodiment, a method of improving insulin sensitivity in a host in need thereof is provided, including administering an effective amount of a compound of Formula A, B, I or II, or a monosuccinic acid ester of probucol, or a pharmaceutically acceptable salt, ester, pharmaceutically acceptable derivative, or prodrug thereof.

In another embodiment, a method of treatment of a host who has been diagnosed with a pre-diabetes condition is provided, including administering an effective amount of a compound of Formula A, B, I or II, or a monosuccinic acid ester of probucol, or a pharmaceutically acceptable salt, ester, pharmaceutically acceptable derivative, or prodrug thereof.

In one embodiment, the invention provides methods and pharmaceutical compositions for the prophylaxis or treatment of diabetes-related disorders in a host comprising administering an effective amount of a compound of Formula A, B, I or II, or a monosuccinic acid ester of probucol, or a pharmaceutically acceptable salt, ester, pharmaceutically acceptable derivative, or prodrug thereof.

In one embodiment, the invention provides methods and pharmaceutical compositions for treatment or prophylaxis of kidney failure in a host, in particular humans, including administering an effective amount of a compound of Formula A, B, I or II, or a monosuccinic acid ester of probucol, or a pharmaceutically acceptable salt, ester, pharmaceutically acceptable derivative, or prodrug thereof.

In one aspect of the invention a method or composition for the treatment or prophylaxis of diabetes, a pre-diabetic condition or a diabetes related disorder is provided, which comprises administering to a patient in need of such treatment an effective amount of a compound of Formula A, B, I or II or pharmaceutically acceptable salt, ester, pharmaceutically acceptable derivative, or prodrug thereof in combination or alternation with at least one compound selected from a biguanide, a thiazolidinedione, a sulfonylurea, a benzoic acid derivative and a alpha-glucosidase inhibitor.

In certain embodiments, the host in need of treatment has been diagnosed with low glucose tolerance, insulin resistance, retinopathy, nephropathy, neuropathy, Syndrome X, or other disorders where insulin resistance is a component.

In certain embodiments, a method for reducing the risks of adverse sequelae associated with metabolic syndrome in a host in need of such treatment is provided which comprises administering to the patient a therapeutically effective amount of a compound of Formula A, B, I or II or pharmaceutically acceptable salt, ester, pharmaceutically acceptable derivative, or prodrug thereof. In a specific embodiment, the compound is a monosuccinic acid ester of probucol.

In one aspect of the invention a method or composition for the treatment or prophylaxis of diabetes, a pre-diabetic condition or a diabetes related disorder is provided, which comprises administering to a patient in need of such treatment an effective amount of a monosuccinic acid ester of probucol, or pharmaceutically acceptable salt, ester, pharmaceutically acceptable derivative, or prodrug thereof, In another aspect of the invention a method or composition for the treatment or prophylaxis of diabetes, a pre-diabetic condition or a diabetes related disorder is provided, which comprises administering to a patient in need of such treatment an effective amount of a monosuccinic acid ester of probucol, or pharmaceutically acceptable salt, ester, pharmaceutically acceptable derivative, or prodrug thereof, in combination or alternation with at least one compound selected from a biguanide, a thiazolidinedione, a sulfonylurea, a benzoic acid derivative and a alpha-glucosidase inhibitor.

BRIEF DESCRIPTION OF THE FIGURES

FIG. 2 shows graphs of the mean change in blood glucose of diabetics and non-diabetics.

FIG. 3 shows graphs of the absolute change in blood glucose of diabetics and non-diabetics.

FIG. 15 is a table showing the rate of certain events possibly related to diabetic control.

FIG. 17 is a graph of the absolute change in eGFR comparing diabetic to non-diabetic subjects

FIG. 20 are graphs showing the change in glucose for non-diabetic and diabetic subjects from baseline.

DETAILED DESCRIPTION OF THE INVENTION

Figure 1:
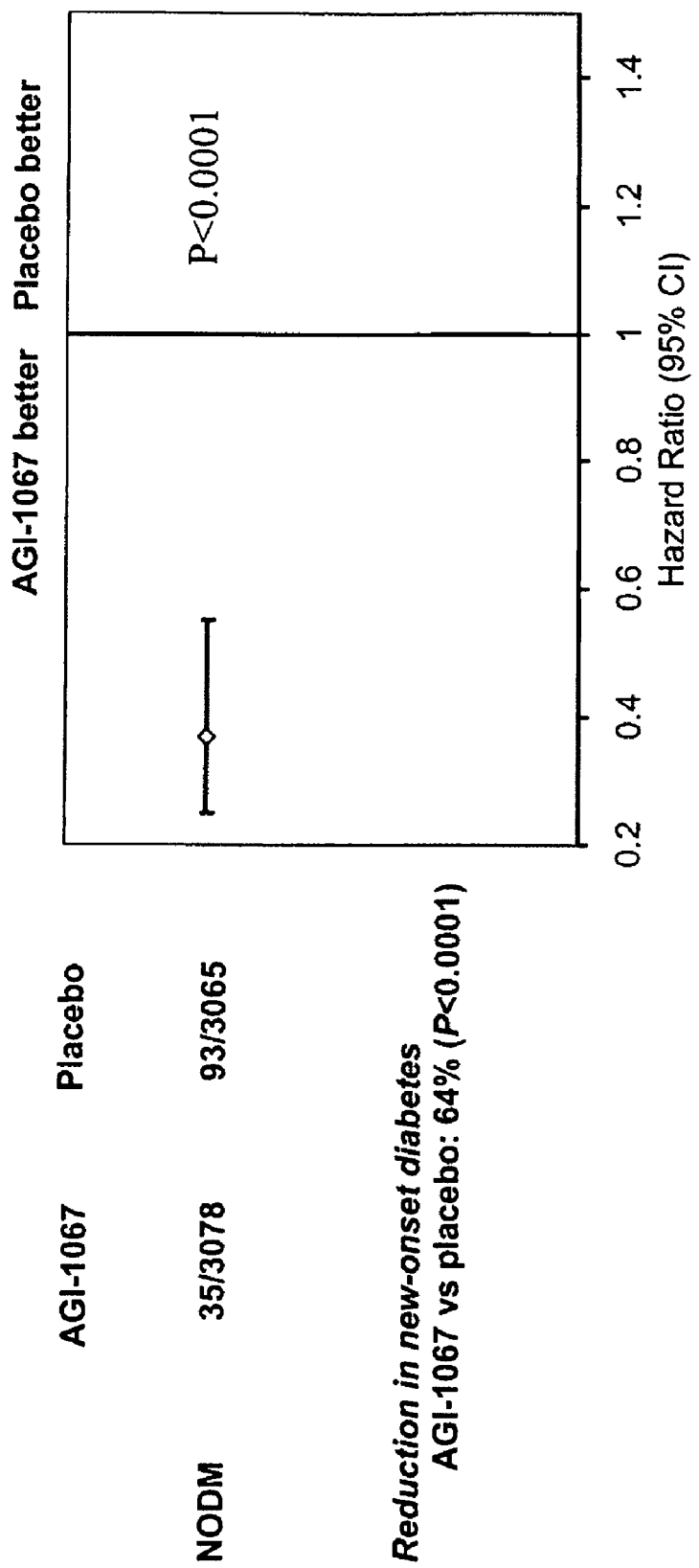
FIG. 1 shows a graph of new onset diabetes mellitus during the trial of AGI1067 (the monosuccinic acid ester of probucol) and placebo.

It has been found that certain probucol monoesters are useful in the treatment or prophylaxis of diabetes and related disorders, in particular in the treatment of type 2 diabetes. It was found that these compounds are useful in reducing the onset of diabetes as well as its progression, in reducing total blood glucose and reducing levels of HbA1c.

Compounds

The invention generally provides a method for the treatment or prophylaxis of diabetes, a pre-diabetes condition or a diabetes related disorder in a host, comprising administering a compound of formula (A) or (B) or more specific formula (I) or (II), as well as the following subembodiments. In general, compounds that can be used in the invention include compounds disclosed in U.S. Pat. No. 6,147,250.

Formula A

In one embodiment, the invention provides a method for the treatment or prophylaxis of diabetes, a pre-diabetes condition or a diabetes related disorder in a host, comprising administering a compound of formula (A)

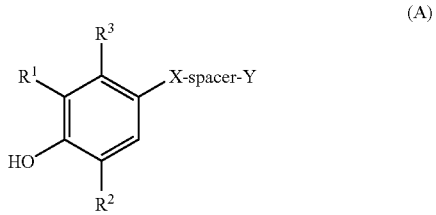

(A)

wherein

X is O, S, SO, SO$_2$, CH$_2$, or NH;

"spacer" is a group selected from the group consisting of —(CH$_2$)$_n$—, —(CH$_2$)$_n$—CO—, —(CH$_2$)$_n$—N—, —(CH$_2$)$_n$—O—, —(CH$_2$)$_n$—S—, —(CH$_2$O)—, —(OCH$_2$)—, —(SCH$_2$)—, —(CH$_2$S)—, -(aryl-O)—, —(O-aryl)-, -(alkyl-O)—, —(O-alkyl)-, —O—C(O)—, —S—C(S)—, —C(O)—O— and —C(S)—S—;

n is 0, 1, 2, 3, 4, 5, 6, 7, 8, 9, or 10;

Y is aryl, heteroaryl, alkyl, alkoxy, alkoxyalkyl, alkylthio, alkylthioalkyl, alkylsulfinyl, alkylsulfinylalkyl, alkylsulfonyl, alkylsulfonylalkyl, wherein any of these groups are optionally substituted, NH$_2$, NHR, NR$_2$, SO$_2$—OH, OC(O)R, C(O)OH, C(O)OR, C(O)NH$_2$, C(O)NHR, C(O)NR$_2$, SO$_2$NH$_2$, SO$_2$NHR, SO$_2$NR$_2$;

R is alkyl, alkenyl, alkynyl, aryl, alkyl-C(O)OH, alkyl-C(O)O-alkyl, alkyl-C(O)O-aryl, alkaryl, aralkyl, heteroaryl, wherein any of these groups are optionally substituted, or when attached to a nitrogen atom, two adjacent R groups may combine to form a ring of 5 to 7 members;

R$^1$ and R$^2$ are independently straight chained, branched, or cyclic alkyl, aryl, heteroaryl, alkaryl, or aralkyl, wherein any of these groups are optionally substituted with halogen, alkyl, nitro, amino, alkylamino, dialkylamino, acyl, or acyloxy; and R$^3$ and R$^4$ are independently a group that does not otherwise adversely affect the desired properties of the molecule, including H, halogen, or R$^1$.

In a more specific embodiment, the compound is of Formula A wherein X is S, SO or SO$_2$; "spacer" is —(CH$_2$)$_n$— or —(CH$_2$)$_n$CO—; Y is aryl, heteroaryl, alkyl, acyloxy, wherein any of these groups are optionally substituted, NH$_2$, NHR or NR$_2$; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; R$^1$ and R$^2$ are independently straight chained, branched or cyclic C$_{1-10}$ alkyl; and R$^3$ and R$^4$ are independently hydrogen, halogen or R$^1$.

In another embodiment of compounds of Formula A, X is S, SO, or SO$_2$; "spacer" is —(CH$_2$)$_n$— or —(CH$_2$)$_n$—CO—; Y is aryl, heteroaryl, alkyl, acyloxy, wherein any of these groups are optionally substituted, NH$_2$, NHR or NR$_2$ wherein R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; R$^1$ and R$^2$ are independently straight chained, branched or cyclic C$_{1-5}$ alkyl; and R$^3$ and R$^4$ are independently H.

In yet another embodiment of Formula A, X is S, SO, or SO$_2$; "spacer" is —(CH$_2$)$_n$— or —(CH$_2$)$_n$—CO—; Y is straight chained, branched or cyclic alkyl, unsubstituted or substituted by one or more OC(O)R, SO$_2$OH, C(O)OH or C(O)OR, aryl which is unsubstituted or substituted by one or more alkyl, alkenyl, alkynyl, halo, nitro, hydroxy, COOH, COOR, CONH$_2$, CONHR, CONR$_2$, —(CH$_2$)$_m$—OH wherein m is 0-10, haloalkyl, mono- or poly-hydroxysubstituted branched alkyl, a carbohydrate group, SO$_2$OH, SO$_2$NH$_2$, SO$_2$NHR, SO$_2$NR$_2$, or OCOR, heteroaryl which is unsubstituted or substituted by one or more alkyl, alkenyl, alkynyl, CH$_2$NH$_2$, CH$_2$NHR, CH$_2$NR$_2$, COOH, COOR, NH$_2$, NHR, NR$_2$, or OCOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; R$^1$ and R$^2$ are independently C$_{1-5}$ alkyl; and R$^3$ and R$^4$ are independently H.

In another embodiment of compounds of Formula A, X is S, SO, or SO$_2$; "spacer" is —(CH$_2$)$_n$— or —(CH$_2$)$_n$—CO—; Y is aryl, aryl which is mono- or polysubstituted by alkyl, alkenyl, alkynyl, halo, nitro, hydroxy, COOH, COOR, CONH$_2$, CONHR, CONR$_2$, —(CH$_2$)$_m$—OH wherein m is 0-10, haloalkyl, mono- or poly-hydroxysubstituted branched alkyl, a carbohydrate group, SO$_2$OH, SO$_2$NH$_2$, SO$_2$NHR, SO$_2$NR$_2$, or OCOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; R$^1$ and R$^2$ are independently C$_{1-5}$ alkyl; and R$^3$ and R$^4$ are independently H.

In another embodiment of compounds of Formula A, X is S, SO, or SO$_2$; "spacer" is —(CH$_2$)$_n$— or —(CH$_2$)$_n$—CO— wherein n is 0-10; Y is phenyl; phenyl which is mono- or polysubstituted by alkyl, alkenyl, alkynyl, halo, nitro, hydroxy, COOH, COOR, CONH$_2$, CONHR, CONR$_2$, —(CH$_2$)$_m$—OH wherein m is 0-10, haloalkyl, mono- or poly-hydroxysubstituted branched alkyl, a carbohydrate group, SO$_2$OH, SO$_2$NH$_2$, SO$_2$NHR, SO$_2$NR$_2$, or OCOR wherein R is alkyl, alkenyl, alkynyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; R$^1$ and R$^2$ are independently C$_{1-5}$ alkyl; R$^3$ and R$^4$ are independently H.

In another embodiment of compounds of Formula A, X is S, SO, or SO$_2$; "spacer" is —(CH$_2$)$_n$— wherein n is 0-10; Y is phenyl; phenyl which is mono- or polysubstituted by alkyl, alkenyl, alkynyl, halo, nitro, hydroxy, COOH, COOR, CONH$_2$, CONHR, CONR$_2$, —(CH$_2$)$_m$—OH wherein m is 0-10, haloalkyl, mono- or poly-hydroxysubstituted branched alkyl, a carbohydrate group, SO$_2$OH, SO$_2$NH$_2$, SO$_2$NHR, SO$_2$NR$_2$, or OCOR; R is alkyl, alkenyl, alkynyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; the R group may be further substituted by alkyl, alkyl-COOH, alkyl-COOalkyl, or alkyl-COOaryl; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$—CO— wherein n is 0-10; Y is phenyl, unsubstituted or substituted with one or more alkyl, alkenyl, alkynyl, halo, nitro, hydroxy, COOH, COOR, $CONH_2$, CONHR, $CONR_2$, —$(CH_2)_m$—OH wherein m is 0-10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkenyl, alkynyl, alkyl-COOH, alkyl-COOalkyl, alkyl-COOaryl, aryl, heteroaryl, nitro-substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is phenyl; phenyl which is mono- or polysubstituted by alkyl, halo, nitro, hydroxy, COOH, COOR, $CONH_2$, CONHR, $CONR_2$, —$(CH_2)_m$—OH wherein m is 0-10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is phenyl; phenyl which is mono- or polysubstituted by alkyl, halo, nitro, hydroxy, COOH, COOR, $CONH_2$, CONHR, $CONR_2$, —$(CH_2)_m$—OH wherein m is 0-10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkyl-COOH, alkyl-COOalkyl, alkyl-COOaryl, or nitro-substituted furanyl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is heteroaryl; heteroaryl which is mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$— wherein n is 0-10; Y is heteroaryl, heteroaryl which is mono- or polysubstituted by alkyl, alkenyl, alkynyl, $CH_2NH_2$, $CH_2NHR$, $CH_2NR_2$, COOH, COOR wherein R is alkyl, alkenyl, alkynyl, aryl, alkyl-COOH, alkyl-COOalkyl, alkyl-COOaryl, heteroaryl, nitro substituted heteroaryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$—CO—; n is 0-10; Y is heteroaryl, unsubstituted or substituted by one or more by alkyl, alkenyl, alkynyl, $CH_2NH_2$, $CH_2NHR$, $CH_2NR_2$, COOH, COOR wherein R is alkyl, alkenyl, alkynyl, aryl, alkyl-COOH, alkyl-COOalkyl, alkyl-COOaryl, heteroaryl, nitro substituted heteroaryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— or —$(CH_2)_n$—CO—; n is 0-10; Y is isoxazolyl or furanyl which may be optionally substituted by mono- or polysubstituted by alkyl, alkenyl, alkynyl, $CH_2NH_2$, $CH_2NHR$, $CH_2NR_2$, COOH, COOR wherein R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is isoxazolyl which may be optionally substituted by mono- or polysubstituted by alkyl, alkenyl, alkynyl, $CH_2NH_2$, $CH_2NHR$, $CH_2NR_2$, COOH, COOR wherein R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is furanyl which may be optionally substituted by mono- or polysubstituted by alkyl, alkenyl, alkynyl, $CH_2NH_2$, $CH_2NHR$, $CH_2NR_2$, COOH, COOR wherein R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is $NH_2$, NHR or $NR_2$ wherein R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is $NH_2$, NHR or $NR_2$ wherein R is alkyl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— wherein n is 0-10; Y is $NH_2$, NHR or $NR_2$ wherein R is alkyl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$—CO— wherein n is 0-10; Y is $NH_2$, NHR or $NR_2$ wherein R is alkyl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or $SO_2$; "spacer" is —$(CH_2)_n$— or —$(CH_2)_n$—CO— wherein n is 0-10; Y is selected from the group consisting of straight chained, branched or cyclic alkyl, straight chained, branched, or cyclic alkyl substituted by OCOR, SO$_2$OH, COOH or COOR, and OCOR, wherein R is alkyl, alkenyl, alkynyl, and aryl, or when attached to a nitrogen atom, two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$— or —(CH$_2$)$_n$—CO— wherein n is 0-10; Y is selected from the group consisting of straight chained, branched or cyclic alkyl, straight chained, branched, or cyclic alkyl substituted by OCOR, SO$_2$OH, COOH or COOR, and OCOR, wherein R is alkyl or two adjacent R groups may combine to form a ring of 5 to 7 members; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$— wherein n is 0-10; Y is selected from the group consisting of straight chained, branched or cyclic alkyl, straight chained, branched, or cyclic alkyl substituted by OCOR, SO$_2$OH, COOH, and COOR, wherein R is alkyl; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$—CO—, wherein n is 0-10; Y is selected from the group consisting of straight chained, branched or cyclic alkyl and straight chained, branched, or cyclic alkyl substituted by OCOR, wherein R is alkyl; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$— or —(CH$_2$)$_n$—CO— wherein n is 0-10; Y is OCOR wherein R is alkyl; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$— wherein n is 0-10; Y is OCOR wherein R is alkyl; $R^1$ and $R^2$ are independently $C_{1-5}$ alkyl; and $R^3$ and $R^4$ are independently H.

In another embodiment of compounds of Formula A, X is S, SO, or SO$_2$; "spacer" is —(CH$_2$)$_n$—CO— wherein n is 0-10; Y is OCOR wherein R is alkyl; $R^1$ and $R^2$ are independently $C_{1-5}$ alkyl; and $R^3$ and $R^4$ are independently H.

In particular embodiments, the compounds useful in the treatment or prophylaxis of diabetes, pre-diabetic disorders or diabetes-related conditions include compounds of formula (A) as follows:

A-1. X=S; $R^1$=t-butyl; $R^2$=t-butyl; $R^3$=H; $R^4$=H; "spacer"=—CH$_2$—; Y=4-carboxymethylphenyl;
A-2. X=S; $R^1$=t-butyl; $R^2$=t-butyl; $R^3$=H; $R^4$=H; "spacer"=—CH$_2$—; Y=4-nitrophenyl;
A-3. X=S; $R^1$=t-butyl; $R^2$=t-butyl; $R^3$=H; $R^4$=H; "spacer"=—(CH$_2$)$_2$—; Y=4-nitrophenyl;
A-4. X=S; $R^1$=t-butyl; $R^2$=t-butyl; $R^3$=H; $R^4$=H; "spacer"=—CH$_2$—; Y=2-carboxyethyl;
A-5. X=S; $R^1$=t-butyl; $R^2$=t-butyl; $R^3$=H; $R^4$=H; "spacer"=—CH$_2$—; Y=3,5-di-t-butyl-4-carboxypropanoyloxyphenyl;
A-6. X=S; $R^1$=t-butyl; $R^2$=t-butyl; $R^3$=H; $R^4$=H; "spacer"=—CH$_2$—; Y=4-carboxyphenyl;
A-7. X=S; $R^1$=t-butyl; $R^2$=t-butyl; $R^3$=H; $R^4$=H; "spacer"=—CH$_2$—; Y=1-acetyloxy-1-methylethyl;
A-8. X=S; $R^1$=t-butyl; $R^2$=t-butyl; $R^3$=H; $R^4$=H; "spacer"=—CH$_2$—; Y=3-nitrophenyl;
A-9. X=S; $R^1$=t-butyl; $R^2$=t-butyl; $R^3$=H; $R^4$=H; "spacer"=—CH$_2$—; Y=2,4-dinitrophenyl;
A-10. X=S; $R^1$=t-butyl; $R^2$=t-butyl; $R^3$=H; $R^4$=H; "spacer"=—CH$_2$—; Y=4-trifluoromethylphenyl;
A-11. X=S; $R^1$=t-butyl; $R^2$=t-butyl; $R^3$=H; $R^4$=H; "spacer"=—CH$_2$—; Y=2-carboxyfuranyl;
A-12. X=S; $R^1$=t-butyl; $R^2$=t-butyl; $R^3$=H; $R^4$=H; "spacer"=—CH$_2$—; Y=4-(N,N-dimethyl)sulfonamidophenyl;
A-13. X=SO; $R^1$=t-butyl; $R^2$=butyl; $R^3$=H; $R^4$=H; "spacer"=—CH$_2$—; Y=4-nitrophenyl;
A-14. X=SO$_2$; $R^1$=t-butyl; $R^2$=t-butyl; $R^3$=H; $R^4$=H; "spacer"=—CH$_2$—; Y=4-nitrophenyl;
A-15. X=S; $R^1$=t-butyl; $R^2$=t-butyl; $R^3$=H; $R^4$=H; "spacer"=—CH$_2$—; Y=4-acetyloxyphenyl;
A-16. X=S; $R^1$=t-butyl; $R^2$=t-butyl; $R^3$=H; $R^4$=H; "spacer"=—CH$_2$—; Y=4-methylphenyl;
A-17. X=S; $R^1$=t-butyl; $R^2$=t-butyl; $R^3$=H; $R^4$=H; "spacer"=—CH$_2$—; Y=4-fluorophenyl;
A-18. X=S; $R^1$=t-butyl; $R^2$=t-butyl; $R^3$=H; $R^4$=H; "spacer"=—CH$_2$—; Y=ethylsulfonic acid;
A-19. X=S; $R^1$=t-butyl; $R^2$=t-butyl; $R^3$=H; $R^4$=H; "spacer"=—CH$_2$—; Y=2-dimethylaminomethyl;
A-20. X=S; $R^1$=t-butyl; $R^2$=t-butyl; $R^3$=H; $R^4$=H; "spacer"=—(CH$_2$)$_3$—; Y=dimethylamino;
A-21. X=S; $R^1$=t-butyl; $R^2$=t-butyl; $R^3$=H; $R^4$=H; "spacer"=—(CH$_2$)$_5$—; Y=acetyloxy;
A-22. X=S; $R^1$=t-butyl; $R^2$=t-butyl; $R^3$=H; $R^4$=H; "spacer"=—CH$_2$—; Y=4-(2-hydroxy)ethylphenyl.

Formula B

In one embodiment, the invention provides a method for the treatment or prophylaxis of diabetes, a pre-diabetes condition or a diabetes related disorder in a host, comprising administering a compound of formula (B):

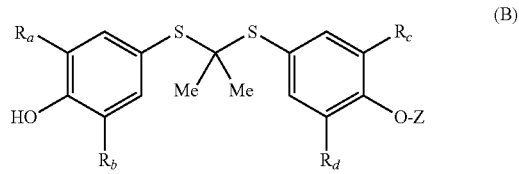

wherein $R_a$, $R_b$, $R_c$, and $R_d$ are independently hydrogen, straight chained, branched (for example, tert-butyl), or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —(CH$_2$)$_n$—$R_e$, —C(O)—$R_g$, and —C(O)—(CH$_2$)$_n$—$R_h$, wherein when each of $R_a$, $R_b$, $R_c$, and $R_d$ are t-butyl, Z cannot be hydrogen, and n is 1, 2, 3, 4, 5, 6, 7, 8, 9 or 10;

$R_e$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH$_2$, NHR, NR$_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, C(O)NH$_2$, C(O)NHR, C(O)NR$_2$, and epoxy;

$R_g$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, and substituted heteroaryl;

$R_h$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, O-phosphate, C(O)$NH_2$, C(O)NHR, C(O)$NR_2$, C(O)-heteroaryl, C(O)-(glycine), C(O)-(arginine), C(O)-(glutamic acid), and C(O)-(lysine);

$R_k$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)R, hydroxy, C(O)$NH_2$, C(O)NHR and C(O)$NR_2$;

R is alkyl, alkenyl, alkynyl, aryl, alkyl-C(O)OH, alkyl-C(O)O-alkyl, alkyl-C(O)O-aryl, heteroaryl, wherein any of these groups are optionally substituted, or when attached to a nitrogen atom, two adjacent R groups may combine to form a ring of 5 to 7 members; and substitutents on the groups defined above in Formula B are selected from the group consisting of alkyl, alkenyl, alkynyl, hydroxy, halo, nitro, amino, alkylamino, dialkylamino, carboxy, aryl, heteroaryl, COOR, CONH$_2$, CONHR, CONR$_2$, haloalkyl, alkoxyalkyl, mono- or polyhydroxyalkyl, CH$_2$—OR, CH$_2$—OH, OCOR, O-phosphate, SO$_2$—NH$_2$, SO$_2$—NHR, SO$_2$—NR$_2$, sulfonic acid and phosphonic acid, any of which can be further substituted.

In an alternative embodiment of Formula B, $R_e$, $R_g$, and $R_h$ can independently be a substituent which improves the water solubility of the compound, including, but not limited to C(O)-spacer-SO$_3$H, C(O)-spacer-SO$_3$M, C(O)-spacer-PO$_3$H$_2$, C(O)-spacer-PO$_3$M$_2$, C(O)-spacer-PO$_3$HM, C(O)-spacer-PO$_4$H, C(O)-spacer-PO$_4$M, SO$_3$M, —PO$_3$H$_2$, —PO$_3$M$_2$, —PO$_3$HM, cyclic phosphates, polyhydroxyalkyl, carbohydrate groups, C(O)-spacer-(O(C$_{1-3}$ alkyl)$_p$)$_q$, —(O(C$_{1-3}$ alkyl)$_p$)$_q$, wherein q or p is independently 1, 2, or 3, M is a metal used to form a pharmaceutically acceptable salt, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

In one embodiment of compounds of Formula B, $R_a$, $R_b$, $R_c$, and $R_d$ are independently hydrogen or straight chained, branched, or cyclic $C_{1-10}$ alkyl; Z is selected from the group consisting of alkyl, substituted alkyl, alkenyl, substituted alkenyl, alkynyl, substituted alkynyl, a carbohydrate group, —(CH$_2$)$_n$—R$_e$, —C(O)—R$_g$, and —C(O)—(CH$_2$)$_n$—R$_h$, and pharmaceutically acceptable salts thereof.

In one embodiment of compounds of Formula B, $R_a$, $R_b$, $R_c$, and $R_d$ are independently hydrogen or straight chained, branched, or cyclic $C_{1-5}$ alkyl; Z is selected from the group consisting of alkyl, substituted alkyl, alkenyl, substituted alkenyl, alkynyl, substituted alkynyl, a carbohydrate group, —(CH$_2$)$_n$—R$_e$, —C(O)—R$_g$, and —C(O)—(CH$_2$)$_n$—R$_h$, and pharmaceutically acceptable salts thereof.

In one embodiment of compounds of Formula B, $R_a$, $R_b$, $R_c$, and $R_d$ are independently hydrogen or straight chained, branched, or cyclic $C_{1-5}$ alkyl; Z is selected from the group consisting of alkyl, substituted alkyl, alkenyl, substituted alkenyl, alkynyl, —CH$_2$-aryl substituted alkynyl, a carbohydrate group, —CH$_2$—NR$_2$, —CH$_2$-alkoxy, —CH$_2$—CHOH, —CH$_2$-substituted aryl, —CH$_2$-alkyl, —CH$_2$-substituted alkyl, —CH$_2$—OCO-alkyl, —CH$_2$—OCO-substituted alkyl, —CH$_2$—COOR, —CH$_2$—CH(OH)CH$_2$NHCH$_2$COOR, —CH$_2$—CH(OH)-substituted oxiranyl (wherein the substituent is selected from the group consisting of hydrogen, CH$_2$OH, CH$_2$OCHOH-oxiranyl), —CO-aryl, —CO-substituted aryl, —CO-heteroaryl, —CO-substituted heteroaryl, —CO—(CH$_2$)$_n$—COOR, —CO—(CH$_2$)$_m$—OH, —CO—(CH$_2$)$_n$—O-phosphate, —CO—(CH$_2$)$_n$—CO—NR$_2$, —CO—(CH$_2$)$_n$-aryl, —CO—(CH$_2$)$_n$— substituted aryl, —CO—(CH$_2$)$_n$-heteroaryl, —CO—(CH$_2$)$_n$-substituted heteroaryl, —CO—(CH$_2$)$_n$—CONH(CH$_2$)COOR, —CO—(CH$_2$)$_n$—CON((CH$_2$)COOR)$_2$, monosaccharides, and cyclic monosaccharides, and pharmaceutically acceptable salts thereof.

In one embodiment of compounds of Formula B, $R_a$, $R_b$, $R_c$, and $R_d$ are independently hydrogen or straight chained, branched, or cyclic $C_{1-5}$ alkyl; Z is selected from the group consisting of alkyl, hydroxy alkyl, polyhydroxy alkyl, alkenyl, hydroxy alkenyl, acyl-substituted alkenyl, alkoxy alkyl, nitrophenylalkyl, aminophenylalkyl, alkylaminophenylalkyl, dialkylaminophenylalkyl, aminoalkyl, alkylaminoalkyl, dialkylaminoalkyl, carboxyalkyl, acyloxyalkyl, oxiranyl-substituted hydroxyalkyl, hydroxyalkyl-substituted oxiranyl-methylene, oxiranyl-substituted hydroxyalkoxyalkyl oxiranylmethylene, oxiranylmethylene, carboxyalkylaminohydroxyalkyl, alkoxyhydroxyalkyl, glucopyranosyl, galactopyranosyl, N,N-diacylalkylaminohydroxyalkyl, carboxyalkylaminopolyhydroxyalkyl, (amino)(carboxy)alkylaminohydroxyalkyl, acyloxyhydroxyalkyl, polyhydroxyalkylaminohydroxyalkyl, CO-carboxyalkyl, CO-nitrofuranyl, CO-hydroxyalkyl, CO-polyhydroxyalkyl, CO-amidoalkyl, CO-aminoalkyl, CO-alkylaminoalkyl, CO-dialkylaminoalkyl, CO-acylalkyl, CO-alkoxycarbonylalkyl, CO-tetrazolylalkyl, CO-(acyl)(amino)alkylamino, dialkoxycarbonylalkylamidoalkyl, and CO-hydroxyphenyloxyphosphonoxyalkyl, or pharmaceutically acceptable salts thereof.

In one embodiment of Formula B, Z is (i) $C_{1-10}$alkyl or substituted $C_{1-10}$alkyl, terminated by sulfonic acid, (ii) $C_{1-10}$alkyl or substituted $C_{1-10}$alkyl, terminated by phosphonic acid, (iii) substituted or unsubstituted $C_{1-10}$alkyl-O—C(O)—$C_{1-10}$alkyl, (iv) straight chained polyhydroxylated $C_{3-10}$ alkyl; (v) —(CR$_{m2}$)$_{1-6}$—COOH, wherein $R_m$ is independently hydrogen, halo, amino, or hydroxy; or (vi) —(CR$_{m2}$)$_{1-6}$—X, wherein X is aryl, heteroaryl, or heterocycle, wherein $R_m$ is independently hydrogen, halo, amino, or hydroxy.

In particular embodiment of compounds of Formula B for use in the treatment of diabetes, pre-diabetic conditions or diabetes-related disorders:

B-1. $R_a$=t-butyl, $R_b$=t-butyl, $R_c$=t-butyl, and $R_d$=t-butyl; Z=4-nitrophenyl;

B-2. $R_a$=t-butyl, $R_b$=t-butyl, $R_c$=t-butyl, and $R_d$=t-butyl; Z=CO—(CH$_2$)$_2$—COOH;

B-3. $R_a$=t-butyl, $R_b$=t-butyl, $R_c$=t-butyl, and $R_d$=t-butyl; Z=CO-(5-nitrofuran-2-yl);

B-4. $R_a$=t-butyl, $R_b$=t-butyl, $R_c$=t-butyl, and $R_d$=t-butyl; Z=3-carboxypropyl;

B-5. $R_a$=1-methylethyl, $R_b$=t-butyl, $R_c$=methyl, and $R_d$=methyl; Z=4-aminobutyl;

B-6. $R_a$=t-butyl, $R_b$=t-butyl, $R_c$=t-butyl, and $R_d$=t-butyl; Z=4-aminobutyl;

B-7. $R_a$=t-butyl, $R_b$=t-butyl, $R_c$=t-butyl, and $R_d$=t-butyl; Z=3-hydroxypropanoyl;

B-8. $R_a$=t-butyl, $R_b$=t-butyl, $R_c$=t-butyl, and $R_d$=t-butyl; Z=t-butylcarbonyloxymethyl;

B-9. $R_a$=t-butyl, $R_b$=t-butyl, $R_c$=H, and $R_d$=H; Z=4-aminobutyl;

B-10. $R_a$=t-butyl, $R_b$=t-butyl, $R_c$=H, and $R_d$=H; Z=3-carboxypropyl;

B-11. $R_a$=t-butyl, $R_b$=t-butyl, $R_c$=t-butyl, and $R_d$=t-butyl; Z=carboxymethyl;
B-12. $R_a$=t-butyl, $R_b$=t-butyl, $R_c$=t-butyl, and $R_d$=t-butyl; Z=2-(CONH$_2$)ethanoyl;
B-13. $R_a$=t-butyl, $R_b$=t-butyl, $R_c$=t-butyl, and $R_d$=t-butyl; Z=CO-aminomethyl;
B-14. $R_a$=t-butyl, $R_b$=t-butyl, $R_c$=t-butyl, and $R_d$=t-butyl; Z=CO-(3-carboxypropyl);
B-15. $R_a$=t-butyl, $R_b$=t-butyl, $R_c$=t-butyl, and $R_d$=t-butyl; Z=CO-(2-methoxycarbonylethyl);
B-16. $R_a$=t-butyl, $R_b$=t-butyl, $R_c$=t-butyl, and $R_d$=t-butyl; Z=CO-aminoethyl;
B-17. $R_a$=t-butyl, $R_b$=t-butyl, $R_c$=t-butyl, and $R_d$=t-butyl; Z=CO-4-carboxybutyl;
B-18. $R_a$=t-butyl, $R_b$=t-butyl, $R_c$=t-butyl, and $R_d$=t-butyl; Z=2-carboxyethyl;
B-19. $R_a$=t-butyl, $R_b$=t-butyl, $R_c$=H, and $R_d$=H; Z=CO-2-carboxyethyl;
B-20. $R_a$=t-butyl, $R_b$=t-butyl, $R_c$=t-butyl, and $R_d$=t-butyl; Z=CO-ammonium methyl (chloride)
B-21. $R_a$=t-butyl, $R_b$=t-butyl, $R_c$=t-butyl, and R=t-butyl; Z=2-hydroxy-2-oxiranyl-ethyl;
B-22. $R_a$=t-butyl, $R_b$=t-butyl, $R_c$=t-butyl, and $R_d$=t-butyl; Z=3-hydroxymethyloxirany-2-ylmethyl;
B-23. $R_a$=t-butyl, $R_b$=t-butyl, $R_c$=t-butyl, and $R_d$=t-butyl; Z=3-(2-hydroxy-2-oxiranyl)ethoxyoxiran-2-ylmethyl;
B-24. $R_a$=t-butyl, $R_b$=t-butyl, $R_c$=t-butyl, and $R_d$=t-butyl; Z=oxiranylmethyl;
B-25. $R_a$=t-butyl, $R_b$=t-butyl, $R_c$=t-butyl, and $R_d$=t-butyl; Z=2-hydroxy-3-carboxymethylaminopropyl;
B-26. $R_a$=t-butyl, $R_b$=t-butyl, $R_c$=t-butyl, and $R_d$=t-butyl; Z=2,3,4-trihydroxybutyl;
B-27. R=t-butyl, $R_b$=t-butyl, $R_c$=t-butyl, and $R_d$=t-butyl; Z=2-hydroxy-3-ethoxypropyl;
B-28. $R_a$=t-butyl, $R_b$=t-butyl, R=t-butyl, and $R_d$=t-butyl; Z=2,3-dihydroxypropyl;
B-29. $R_a$=t-butyl, $R_b$=t-butyl, $R_c$=t-butyl, and $R_d$=t-butyl; Z=ethyl;
B-30. $R_a$=t-butyl, $R_b$=t-butyl, $R_c$=t-butyl, and $R_d$=t-butyl; Z=2-ethoxycarbonylethenyl;
B-31. $R_a$=t-butyl, $R_b$=t-butyl, $R_c$=t-butyl, and $R_d$=t-butyl; Z=4-N,N-dimethylaminophenethyl;
B-32. R=t-butyl, $R_b$=t-butyl, $R_c$=H, and $R_d$=H; Z=CO-3-carboxypropyl;
B-33. $R_a$=t-butyl, $R_b$=t-butyl, $R_c$=t-butyl, and $R_d$=t-butyl; Z=CO-2-carboxyethyl (L-arginine ester);
B-34. $R_a$=t-butyl, $R_b$=t-butyl, $R_c$=t-butyl, and $R_d$=t-butyl; Z=3-methoxycarbonylpropyl;
B-35. $R_a$=t-butyl, $R_b$=t-butyl, $R_c$=t-butyl, and $R_d$=t-butyl; Z=2-carboxyethenyl;
B-36. $R_a$=t-butyl, $R_b$=t-butyl, $R_c$=t-butyl, and $R_d$=t-butyl; Z=galactopyranosylmethyl;
B-37. $R_a$=t-butyl, $R_b$=t-butyl, $R_c$=t-butyl, and $R_d$=t-butyl; Z=3-(N—N-diethylamino)propyl;
B-38. $R_a$=t-butyl, $R_b$=t-butyl, $R_c$=t-butyl, and $R_d$=t-butyl; Z=3-ethoxycarbonylpropenyl;
B-39. $R_a$=t-butyl, $R_b$=t-butyl, $R_c$=t-butyl, and $R_d$=t-butyl; Z=carboxymethylaminocarbonylmethyl;
B-40. $R_a$=t-butyl, $R_b$=t-butyl, $R_c$=t-butyl, and $R_d$=t-butyl; Z=1,3-dicarboxypropylaminocarbonylmethyl;
B-41. $R_a$=t-butyl, $R_b$=t-butyl, $R_c$=t-butyl, and $R_d$=t-butyl; Z=2-hydroxy-3-(1,3-diethoxycarbonyl)propylaminopropyl;
B-42. $R_a$=t-butyl, $R_b$=t-butyl, $R_c$=t-butyl, and $R_d$=t-butyl; Z=2,3-dihydroxy-4-carboxymethylaminobutyl;
B-43. $R_a$=t-butyl, $R_b$=t-butyl, $R_c$=t-butyl, and $R_d$=t-butyl; Z=2-hydroxy-3-(5-amino-5-carboxy)propylaminopropyl;
B-44. $R_a$=t-butyl, $R_b$=t-butyl, $R_c$=t-butyl, and $R_d$=t-butyl; Z=4-ethylcarbonyloxybutyl;
B-45. $R_a$=t-butyl, $R_b$=t-butyl, $R_c$=t-butyl, and $R_d$=t-butyl; Z=4-hydroxybutyl;
B-46. $R_a$=t-butyl, $R_b$=t-butyl, $R_c$=t-butyl, and $R_d$=t-butyl; Z=glucopyranosylmethyl;
B-47. $R_a$=t-butyl, $R_b$=t-butyl, $R_c$=t-butyl, and R&=t-butyl; Z=CO-3-tetrazolylpropyl;
B-48. $R_a$=t-butyl, $R_b$=t-butyl, $R_c$=t-butyl, and $R_d$=t-butyl; Z=3-hydroxypropenyl;
B-49. $R_a$=t-butyl, $R_b$=t-butyl, $R_c$=t-butyl, and $R_d$=t-butyl; Z=CH$_2$CONH—(CH$_2$)CH(NH$_2$)COOH;
B-50. $R_a$=t-butyl, $R_b$=t-butyl, $R_c$=t-butyl, and $R_d$=t-butyl; Z=CH$_2$CONHCH(COOet)CH$_2$CH$_2$(COOet);
B-51. $R_a$=t-butyl, $R_b$=t-butyl, $R_c$=t-butyl, and $R_d$=t-butyl; Z=glucopyranosylmethyl;
B-52. $R_a$=t-butyl, $R_b$=t-butyl, $R_c$=t-butyl, and $R_d$=t-butyl; Z=2,3,4,5,6-pentahydroxyhexane;
B-53. $R_a$=t-butyl, $R_b$=t-butyl, $R_c$=t-butyl, and $R_d$=t-butyl; Z=CO-3-(2-hydroxyphenyloxypbosphoxy)propyl;
B-54. $R_a$=t-butyl, $R_b$=t-butyl, $R_c$=t-butyl, and $R_d$=t-butyl; Z=CO-2,2-dimethyl-3-hydroxypropyl;
B-55. $R_a$=t-butyl, $R_b$=t-butyl, $R_c$=t-butyl, and $R_d$=t-butyl; Z=2-hydroxy-3-acetoxypropyl;
B-56. $R_a$=t-butyl, $R_b$=t-butyl, $R_c$=t-butyl, and $R_d$=t-butyl; Z=2-acetoxy-3-hydroxypropyl;
B-57. $R_a$=t-butyl, $R_b$=t-butyl, $R_c$=t-butyl, and $R_d$=t-butyl; Z=CH$_2$CH(OH)CH$_2$NH (2,3,4,5,6)-pentahydroxyhexane.

Formula I

In one embodiment, the invention provides a method for the treatment or prophylaxis of diabetes, a pre-diabetes condition or a diabetes related disorder in a host, comprising administering an effective amount of a compound of Formula I:

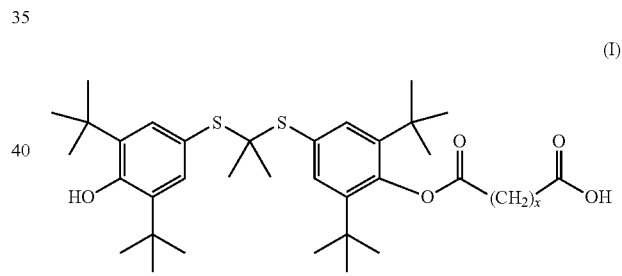

wherein x is selected from 1, 2, 3 or 4;
or a pharmaceutically acceptable salt, ester, pharmaceutically acceptable derivative, or prodrug thereof.

In one sub-embodiment, x is 2. In another subembodiment, x is 3. In one subembodiment, the host is a human. In a particular subembodiment, the compound is a monosuccinic acid ester of probucol or a pharmaceutically acceptable salt, ester, pharmaceutically acceptable derivative, or prodrug thereof.

In a specific subembodiment, the compound is a monosuccinic acid ester of probucol of the structure:

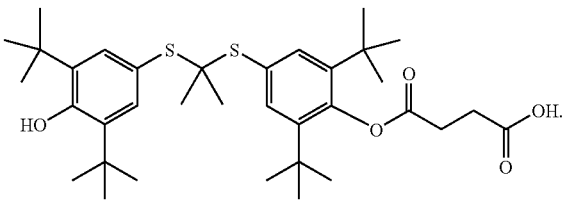

Formula II

In a more particular embodiment, the invention provides a method for the treatment or prophylaxis of diabetes, a pre-diabetes condition or a diabetes related disorder in a host, comprising administering a compound of Formula II:

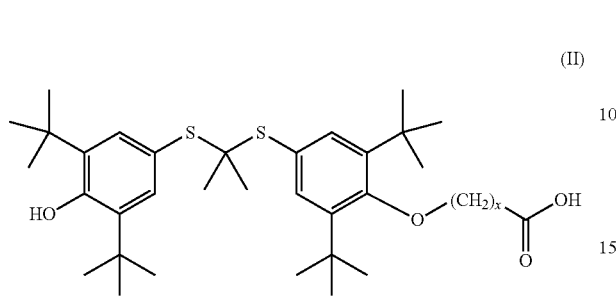

(II)

wherein x is selected from 1, 2, 3 or 4;
or a pharmaceutically acceptable salt, ester, pharmaceutically acceptable derivative, or prodrug thereof. In a particular embodiment, x is 1. In one sub-embodiment, x is 2. In another subembodiment, x is 3. In a further sub-embodiment, x is 4.

In one embodiment, the compound is of the structure:

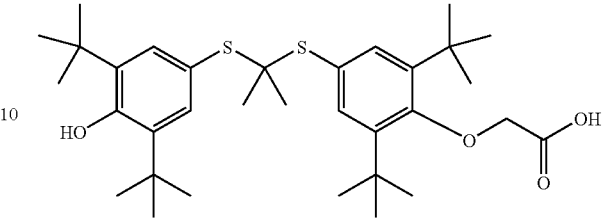

or a pharmaceutically acceptable salt, ester, pharmaceutically acceptable derivative, or prodrug thereof.

Specific compounds to be used in the methods or compositions of the present invention include those listed in Table I:

TABLE I

| | |
|---|---|
| 2,6-di-tert-butyl-4-thio(4'(methyl)phenylacetic acid))phenol | Butanoic acid, 4-[4-[[1-[[3,5-bis(1,1-dimethylethyl)-4-hydroxyphenyl]thio]-1-methylethyl]thio]-2,6-bis(1,1-dimethylethyl)phenoxy]- |
| 2,6-di-tert-butyl-4-thio(4'-nitrobenzyl)phenol | Butanedioic acid, (1-methylethylidine)bis[thio[2,6-bi(1,1-dimethylethyl)-4,1-phenylene}} ester, |
| 2,6-di-tert-butyl-4-thio(4'-nitrophenethyl)phenol | Glycine, (1-methylethylidene)bis [bis [thio2,6-bis (1,1-dimethylthyl)-4,1-phenylene]] ester, dihydrochloride |
| 2,6-di-tert-butyl-4-thio(butanoic acid)phenol | Oxiranemethanol, α-[[4-[[1-[[3,5-bis(1,1-dimethylethyl)-4-hydroxyphenyl]thio]-1-methylethyl]thio]-2,6-bis(1,1-dimethylethyl)phenoxy]methyl]-; |
| 2,6-di-tert-butyl-4-thio(3',5'-ditert-butyl,4'-hydroxyphenyl butanedioic acid ester)phenol | Oxiranemethanol, 3-[[4-[[1-[[3,5-bis(1,1-dimethylethyl)-4-hydroxyphenyl]thio]-1-methylethyl]thio]-2,6-bis(1,1-dimethylethyl)phenoxy]methyl]-; |
| 2,6-di-tert-butyl-4-thio(4'(methyl)benzoic acid)phenol | Oxiranemethanol, α-[[[3-[[4-[[1-[[3,5-bis(1,1-dimethylethyl)-4-hydroxyphenyl]thio]-1-methylethyl]thio]-2,6-bis(1,1-dimethylethyl)phenoxy]methyl]oxiranyl]methoxy]methyl]- |
| 2,6-di-tert-butyl-4-thio(2'-acetoxy,2'-methylpropyl)phenol | Phenol, 4-[[1-[[3,5-bis(1,1-dimethylethyl)-4-(oxiranylmethoxy)phenyl]thio]-1-methylethyl]thio]-2,6-bis(1,1-dimethylethyl)- |
| 2,6-di-tert-butyl-4-thio(3'-nitrobenzyl)phenol | Glycine, N-[3-[4-[[1-[[3,5-bis(1,1-dimethylethyl)-4-hydroxyphenyl]thio]-1-methylethyl]thio]-2,6-bis(1,1-dimethylethyl)phenoxy]2-hydroxypropyl]- |
| 2,6-di-tert-butyl-4-thio(2',4'-dinitrobenzyl)phenol | 1,2,3-Butanetriol, 4-[4-[[1-[[3,5-bis(1,1-dimethylethyl)-4-hydroxyphenyl]thio]-1-methylethyl]thio]-2,6-bis(1,1-dimethylethyl)phenoxy]-2-hydroxypropyl]- |
| (2,6-di-tert-butyl-4-thio(4'-(trifluoromethyl)benzyl)phenol | Phenol, 4-[[1-[[3,5-bis(1,1-dimethylethyl)-4-(3-ethoxy-2-hydroxypropoxy)phenyl]thio]-1-methylethyl]thio]-2,6-bis(1,1-dimethylethyl)-; |
| 2,6-di-tert-butyl-4-thio((2'-furancarboxylic acid)-5-methyl)phenol | 1,2-Propanediol, 3-[4-[[1-[[3,5-bis(1,1-dimethylethyl)-4-hydroxyphenyl]thio]-1-methylethyl]thio]-2,6-bis(1,1-dimethylethyl)phenoxy]- |
| 2,6-di-tert-butyl-4-thio(4'-methyl-N,N-dimethylbenzenesulfonamide)phenol | Phenol, 4-[[1-[[3,5-bis(1,1-dimethylethyl)-4-ethoxyphenyl]thio]-1-methylethyl]thio]-2,6-bis(1,1-dimethylethyl)- |

TABLE I-continued

| | |
|---|---|
| 2,6-di-tert-butyl-4-sulfinyl(4'-nitrobenzyl)phenol | 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, ethyl ester, (E)- |
| 2,6-di-tert-butyl-4-(sulfonyl-(4'-nitrobenzyl))phenol | Butanedioic acid, mono[4-[[1-[[3,5-bis(1,1-dimethylethyl)-4-methoxyphenyl]thio]1-methylethyl]thio]-2,6-bis(1,1-dimethylethyl)phenyl] ester |
| 2,6-di-tert-butyl-4-thio(4'-acetoxybenzyl)phenol | Phenol, 4-[[1-[[4-[2-[4-(dimethylamino)phenyl]ethoxy]-3,5-bis(1,1-dimethylethyl)phenyl]thio]-1-methylethyl]thio]-2,6-bis(1,1-dimethylethyl)- |
| 2,6-di-tert-butyl-4-thio(4'-methylbenzyl)phenol | Benzenamine, 4,4'-[(1-methylethylidene)bis[thio[2,6-bis(1,1-dimethylethyl)-4,1-phenylene]oxy-2,1-ethanediyl]]bis[N,N-dimethyl- |
| 2,6-di-tert-butyl-4-thio(4'-fluorobenzyl)phenol | L-Arginine, mono[4-[[1-[[3,5-bis(1,1-dimethylethyl)-4-hydroxyphenyl]thio]-1-methylethyl]thio]-,6-bis(1,1-dimethylethyl)phenyl butanedioate] |
| 2,6-di-tert-butyl-4-thio(3'-propanesulfonic acid)phenol | pentanedioic acid, 4-[[1-[[3,5-bis(1,1-dimethylethyl)-4-hydroxyphenyl]thio]-1-methylethyl]thio]-,6-bis(1,1-dimethylethyl)phenyl methyl ester |
| 2,6-di-tert-butyl-4-thio(5'-methyl-2'-((dimethylamino)methyl)furan)phenol | 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, (E)- |
| 2,6-di-tert-butyl-4-thio(3'-(dimethylamino)propyl))phenol | α-D-Galactopyranose, 6-O-[4-[[1-[[3,5-bis(1,1-dimethylethyl)-4-hydroxyphenyl]thio]-1-methylethyl]thio]-2,6-bis(1,1-dimethylethyl)phenyl]-1,2:3,4-bis-O-(1-methylethylidene) |
| 2,6-di-tert-butyl-4-thio((1'-(acetoxy))pentyl)phenol | Phenol, 4-[[1-[[4-[3-(dimethylamino)propoxy]-3,5-bis(1,1-dimethylethyl)phenyl]thio]-1-methylethyl]thio]-2,6-bis(1,1-dimethylethyl)- |
| 2,6-di-tert-butyl-1-methoxy-4-thio(4'-trifluoromethyl)benzyl) benzene | Glycine, N-[[4-[[1-[[3,5-bis(1,1-dimethylethyl)-4-hydroxyphenyl]thio]-1,methylethyl]thio]-2,6-bis(1,1-dimethylethyl)phenoxy]acetyl]- |
| 2,6-di-tert-butyl-4-thio(4'-(methyl)phenylethyl alcohol))phenol | Glutamic acid, N-[[4-[[1-[[3,5-bis(1,1-dimethylethyl)-4-hydroxyphenyl]thio]-1-methylethyl]thio]-2,6-bis(1,1-dimethylethyl)phenoxy]acetyl]- |
| Phenol, 4-[[1-[3,5-bis(1,1-dimethylethyl)4-[(4-nitrophenyl)methoxy]phenyl]thio]-1-methylethyl]thio]2,6-bis(1,1-dimethylethyl)- | L-Glutamic acid, N-[3-[4-[[1-[[3,5-bis(1,1-dimethylethyl)-4-hydroxyphenyl]thio]-1-methylethyl]thio]-2,6-bis(1,1-dimethylethyl)phenoxy]-2-hydroxypropyl]-di-, diethyl ester |
| Butanedioic acid, mono [4-[[1-[[3,5-bis(1,1-dimethylethyl)-4-hydroxyphenyl]thio]-1-methylethyl]thio]2,6-bis(1,1-dimethylethyl)phenyl] ester | Glycine, N-[4-[4[[1-[[3,5-bis (1,1-dimethylethyl)-4-hydroxphenyl]thio]-1-methylethyl]thio]-2,6-bis (1,1-dimethylethyl)phenoxy]-2,3-dihydroxybutyl]- |
| 2-Furancarboxylic acid, 5-nitro-, 4-[[1-[[3,5-bis(1,1-dimethylethyl)-4-hydroxyphenyl]thio]-1-methylethyl]thio]-2,6-bis(1,1-dimethylethyl)phenyl ester | L-Lysine, $N^6$-[3-[4-[[1-[[3,5-bis(1,1-dimethylethyl)-4-hydroxyphenyl]thio]-1-methylethy]thio]-2,6-bis (1,1-dimethylethyl)phenoxy]-2-hydroxypropyl]- |
| Butanoic acid, 4-[4-[[1-[[3,5-bis(1,1-dimethylethyl)-4-hydroxyphenyl]thio]-1-methylethyl]thio]2,6-dimethylphenoxy]- | 2-Propenoic acid, 4-[4-[[1-[[3,5-bis(1,1-dimethylethyl)-4-hydroxyphenyl]thio]-1-methylethyl]thio]-2,6-bis(1,1-dimethylethyl)phenoxy] butyl ester |
| Phenol, 4-[[1-[[4-(4-aminobutoxy)-3,5-bis(1,1-dimethylethyl)phenyl]thio]-1-methylethyl]thio]2,6-bis(1,1-dimethylethyl)- | Phenol, 4-[[1-[[3,5-bis(1,1-dimethylethyl)-4-(4-hydroxybutoxy)phenyl] thio]-1-methylethyl]thio]-2,6-bis(1,1-dimethylethyl)- |
| Phenol, 4-[[1-[[4-(4-aminobutoxy)-3,5-bis(1,1-dimethylethyl)phenyl]thio]-1-methylethyl]thio]2,6-bis(1,1-dimethylethyl)- | β-D-Glucopyranose, 6-O-[4-[[1-[[3,5-bis(1,1-dimethylethyl)-4-hydroxyphenyl]thio]-1-methylethyl]thio]-2,6-bis(1,1-dimethylethyl)phenyl]- |
| Butanoic acid, 4-hydorxy-, 4-[[1-[[3,5-bis(1,1-dimethylethyl)-4-hydroxyphenyl]thio]-1-methylethyl]thio]-2,6-bis(1,1-dimethylethyl)phenyl ester | 1-H-Tetrazole-1-butanoic acid, 4-[[1-[[3,5-bis(1,1-dimethylethyl)-4-hydroxyphenyl]thio]-1-methylethyl]thio]-2,6-bis(1,1-dimethylethyl)phenyl ester |

TABLE I-continued

Propanoic acid, 2,2-dimethyl-, [4-[[1-[[3,5-bis(1,1-dimethylethyl)-4-hydroxyphenyl]thio]-1-methylethyl]thio]-2,6-bis(1,1-dimethylethyl)phenoxy]methyl ester Phenol, 4-[[1-[[4-(4-aminobutoxy)phenyl]thio]-1-methylethyl]thio]-2,6-bis(1,1-dimethylethyl)-

Butanoic acid, 4-[4-[[1-[[3,5-bis(1,1-dimethylethyl)-4-hydroxyphenyl]thio]-1-methylethyl]thio]phenoxy]-

Acetic acid, [4-[[1-[[3,5-bis(1,1-dimethylethyl)-4-hydroxyphenyl]thio]-1-methylethyl]thio]2,6-bis(1,1-dimethylethyl)phenoxy]-

Butanoic acid, 4-amino-4-oxo-, 4-[[1-[[3,5-bis(1,1-dimethylethyl)-4-hydroxyphenyl]thio]-1-methylethyl]thio]-2,6-bis(1,1-dimethylethyl)phenyl ester Glycine, 4-[[1-[[3,5-bis(1,1-dimethylethyl)-4-hydroxyphenyl]thio]-1-methylethyl]thio]-2,6-dimethylphenyl ester Butanedioic acid, mono[4-[[1-[[3,5-bis(1,1-dimethylethyl)-4-hydroxyphenyl]thio)-1-methylethyl}-2,6-dimethylphenyl] ester Butanedioic acid, mono[4-[[1-[[3,5-bis(1,1-dimethylethyl)-4-hydroxyphenyl]thio)-1-methylethyl}thio-2,6-bis(1,1-dimethylethyl)phenyl methyl ester Glycine, 4-[[1-[[3,5-bis(1,1-dimethylethyl)-4-hydroxyphenyl]thio]-1-methylethyl]thio]-2,6-bis(1,1-dimethylethyl)phenyl ester Phenol, 4-[[1-[[3,5-bis(1,1-dimethylethyl)-4-[[3-hydroxy-1-propenyl)oxy]phenyl]thio]-1-methylethyl]thio]-2,6-bis(1,1-dimethylethyl)-

L-Lysine, $N^6$-[[4-[[1-[[3,5-bis(1,1-dimethylethyl)-4-hydroxyphenyl]thio]-1-methylethyl]thio]-2,6-bis(1,1-dimethylethyl)phenoxy]acetyl]-

D-Glucopyranose, 6-O-[4-[[1-[[3,5-bis(1,1-dimethylethyl)-4-hydroxyphenyl]thio]-1-methylethyl]thio]-2,6-bis(1,1-dimethylethyl)phenyl]-

D-Glucitol, 6-O-[4-[[1-[[3,5-bis(1,1-dimethylethyl)-4-hydroxyphenyl]thio]-1-methylethyl]thio]-2,6-bis(1,1-dimethylethyl)phenyl]-

Butanoic acid, 4-[[hydroxy(2-hydroxyphenoxy)phosphinyl]oxy]-4-[[1-[[3,5-bis(1,1-dimethylethyl)-4-hydroxyphenyl]thio]-1-methylethyl]thio]-2,6-bis(1,1-dimethylethyl)phenyl ester Butanoic acid, 4-hydroxy-3,3-dimethyl-, 4-[[1-[[3,5-bis(1,1-dimethylethyl)-4-hydroxyphenyl]thio]-1-methylethyl]thio]-2,6-bis(1,1-dimethylethyl)phenyl ester Butanoic acid, 4-(sulfoxy)-, 1-[4-[[3,5-bis(1,1-dimethylethyl)-4-hydroxyphenyl]thio]-1-methylethyl]thio]-2,6-bis(1,1-dimethylethyl)phenyl]ester Pentanedioic acid, (1-methylethylidene)bis(thio{2,6-bis(1,1-dimethylethyl)-4,1-phenylene)] ester Pentanedioic acid, mono[4-[[1-[[3,5-bis(1,1-dimethylethyl)-4-hydroxyphenyl]thio]-1-methylethyl]thio]-2,6-bis(1,1-dimethylethyl)phenyl] ester

Methods

In one embodiment, a method of prophylaxis of a host at risk of developing diabetes is provided, including administering an effective amount of a compound of Formula A, B, I or II, or a pharmaceutically acceptable salt, ester, pharmaceutically acceptable derivative, or prodrug thereof.

In a specific embodiment, a method of prophylaxis of a host at risk of developing diabetes is provided, including administering an effective amount of a monosuccinic acid ester of probucol, or a pharmaceutically acceptable salt, ester, pharmaceutically acceptable derivative, or prodrug thereof.

In one embodiment, a method of treatment of a host who has been diagnosed with diabetes is provided, including administering an effective amount of a compound of Formula A, B, I or II, or a pharmaceutically acceptable salt, ester, pharmaceutically acceptable derivative, or prodrug thereof.

In a specific embodiment, a method of treatment of a host who has been diagnosed with diabetes is provided, including administering an effective amount of a monosuccinic acid ester of probucol, or a pharmaceutically acceptable salt, ester, pharmaceutically acceptable derivative, or prodrug thereof.

In one embodiment, the host at risk of or diagnosed with diabetes is at risk of or diagnosed with type 2 diabetes.

In one embodiment, a method of glycemic control in a host in need thereof is provided, including administering an effective amount of a compound of Formula A, B, I or II, or a pharmaceutically acceptable salt, ester, pharmaceutically acceptable derivative, or prodrug thereof.

In a specific embodiment, a method of glycemic control in a host in need thereof is provided, including administering an effective amount of a monosuccinic acid ester of probucol, or a pharmaceutically acceptable salt, ester, pharmaceutically acceptable derivative, or prodrug thereof.

In another embodiment, a method of treatment of a host who has been diagnosed with a pre-diabetes condition is provided, including administering an effective amount of a compound of Formula A, B, I or II, or a pharmaceutically acceptable salt, ester, pharmaceutically acceptable derivative, or prodrug thereof.

In another embodiment, a method of treatment of a host who has been diagnosed with a pre-diabetes condition is provided, including administering an effective amount of a monosuccinic acid ester of probucol, or a pharmaceutically acceptable salt, ester, pharmaceutically acceptable derivative, or prodrug thereof.

In a particular subembodiment, the method is not for treatment of a diabetic vascular disease, diabetic neuropathy, diabetic nephropathy or diabetic retinopathy.

In one embodiment, the invention provides methods and pharmaceutical compositions for the prophylaxis or treatment of diabetes-related disorders in a host comprising administering an effective amount of a compound of Formula A, B, I or II or a pharmaceutically acceptable salt, ester, pharmaceutically acceptable derivative, or prodrug thereof.

In a specific embodiment, the invention provides methods and pharmaceutical compositions for the prophylaxis or treatment of diabetes-related disorders in a host comprising administering an effective amount of a monosuccinic acid ester of probucol, or a pharmaceutically acceptable salt, ester, pharmaceutically acceptable derivative, or prodrug thereof.

In one embodiment, the invention provides methods and pharmaceutical compositions for treatment or prophylaxis of kidney failure in a host, in particular humans, including administering an effective amount of a compound of Formula A, B, I or II, or a pharmaceutically acceptable salt, ester, pharmaceutically acceptable derivative, or prodrug thereof.

In one embodiment, the invention provides methods and pharmaceutical compositions for treatment or prophylaxis of kidney failure in a host, in particular a human, including administering an effective amount of a monosuccinic acid ester of probucol, or a pharmaceutically acceptable salt, ester, pharmaceutically acceptable derivative, or prodrug thereof.

In one embodiment, the invention provides methods and pharmaceutical compositions for lowering glucose levels in a diabetic host, in particular a human, including administering an effective amount of a compound of Formula A, B, I or II, or a pharmaceutically acceptable salt, ester, pharmaceutically acceptable derivative, or prodrug thereof.

In a particular embodiment, the present methods and pharmaceutical compositions are effective in lowering glucose levels in humans afflicted with, or at risk for, type 2 diabetes.

In one embodiment, the invention provides methods and pharmaceutical compositions for the treatment of insulin resistance in diabetic mammals, in particular, humans, including administering an effective amount of a compound of Formula A, B, I or II, or a pharmaceutically acceptable salt, ester, pharmaceutically acceptable derivative, or prodrug thereof. In a particular embodiment, the compound is a monosuccinic acid ester of probucol.

In one embodiment, the invention provides methods and pharmaceutical compositions are effective in lowering glucose in non-diabetic hosts that have impaired glucose tolerance and/or are in a pre-diabetic condition, including administering an effective amount of a compound of Formula A, B, I or II, or a pharmaceutically acceptable salt, ester, pharmaceutically acceptable derivative, or prodrug thereof. In a particular embodiment, the compound is a monosuccinic acid ester of probucol.

In one aspect of the invention a method or composition for the treatment or prophylaxis of diabetes, a pre-diabetic condition or a diabetes related disorder is provided, which comprises administering to a patient in need of such treatment an effective amount of a compound of Formula A, B, I or II or pharmaceutically acceptable salt, ester, pharmaceutically acceptable derivative, or prodrug thereof in combination or alternation with at least one compound selected from the group consisting of a biguanide, a thiazolidinedione, a sulfonylurea, a benzoic acid derivative, a alpha-glucosidase inhibitor, a SGLT2 inhibitor, and INGAP peptide. In another embodiment, the compound of Formula A, B, I or II is provided in combination or alternation with at least one compound selected from the group consisting of: (a) DP-IV inhibitors; (b) insulin sensitizers selected from the group consisting of (i) PPAR agonists and (ii) biguanides; (c) insulin and insulin mimetics; (d) sulfonylureas and other insulin secretagogues; (e) α-glucosidase inhibitors; (f) glucagon receptor antagonists; (g) GLP-1, GLP-1 mimetics, and GLP-1 receptor agonists; (h) GIP, GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPARα/γ dual agonists, (vi) inhibitors of cholesterol absorption, (vii) acyl CoA:cholesterol acyltransferase inhibitors, and (viii) anti-oxidants; (k) PPARδ agonists; (l) antiobesity compounds; (m) an ileal bile acid transporter inhibitor, (n) anti-inflammatory agents excluding glucocorticoids; (o) protein tyrosine phosphatase-1B (PTP-1B) inhibitors; (p) SGLT2 inhibitors; and (q) INGAP peptide. In a specific embodiment the compound of Formula A, B, I or II is a monosuccinic acid ester of probucol.

Compounds of Formula I and pharmaceutically acceptable salts, esters or prodrugs thereof can be used in the manufacture of medicaments for the treatment of diabetes or related disorders in a human or other mammalian patient.

In certain embodiments, the host in need of treatment has been diagnosed with low glucose tolerance, insulin resistance, retinopathy, nephropathy, neuropathy, Syndrome X, or other disorders where insulin resistance is a component.

In other embodiments, the host in need of treatment has been diagnosed with low glucose tolerance, insulin resistance, or Syndrome X.

In certain embodiments, a method for reducing the risks of adverse sequelae associated with metabolic syndrome in a host in need of such treatment is provided which comprises administering to the patient a therapeutically effective amount of a compound of Formula A, B, I or II or pharmaceutically acceptable salt, ester, pharmaceutically acceptable derivative, or prodrug thereof. In a specific embodiment, the compound is a monosuccinic acid ester of probucol.

Any of the compounds described herein for combination or alternation therapy can be administered as any prodrug that upon administration to the recipient, is capable of providing directly or indirectly, the parent compound. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound.

Definitions

Whenever a term in the specification is identified as a range (i.e. $C_{1-4}$ alkyl), the range independently refers to each element of the range. As a non-limiting example, $C_{1-4}$ alkyl means, independently, $C_1$, $C_2$, $C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl", unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of alkyl, halo, hydroxyl, carboxyl, acyl, acyloxy, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. "Lower alkyl" refers to a $C_1$ to $C_5$ saturated straight, branched, or if appropriate, a cyclic (for example, cyclopropyl) alkyl group.

The term "aryl", unless otherwise specified, refers to a radical derived from an aromatic compound by the removal of one hydrogen. The aryl group may be substituted or unsubstituted. Specifically included within the scope of the term aryl are phenyl; biphenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-ditertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like. The aryl group can be optionally substituted with one or more moieties selected from the group consisting of alkyl, halo, hydroxyl, carboxyl, acyl, acyloxy, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991.

The term "aralkyl", unless otherwise specified, refers to an aryl group linked to the molecule through an alkyl group. The term "alkaryl", unless otherwise specified, refers to an alkyl group linked to the molecule through an aryl group.

The term "heteroaryl" or "heteroaromatic" as used herein, refers to an aromatic or unsaturated cyclic moiety that includes at least one sulfur, oxygen, nitrogen or phosphorus in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl. The heteroaryl group can be optionally substituted with one or more moieties selected from the group consisting of hydroxyl, acyl, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in Greene, et al, "Protective Groups in Organic Synthesis," John Wiley and Sons, Second Edition, 1991, hereby incorporated by reference. The term "heterocyclic" refers to a nonaromatic cyclic group that can include alkyl moieties which may be substituted, and wherein there is at least one heteroatom, such as oxygen, sulfur, nitrogen, or phosphorus in the ring. Nonlimiting examples are morpholine, piperidine, piperazine, pyrrolidine, azetidine, and tetrahydrofuran. The heterocyclic group can be optionally substituted with one or more moieties selected from the group consisting of hydroxyl, acyl, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "halo" refers to chloro, bromo, iodo, and fluoro.

The term "alkoxy", unless otherwise specified, refers to a moiety of the structure —O-alkyl.

The term "acyl", unless otherwise specified, refers to a group of the formula C(O)R', wherein R' is substituted or unsubstituted alkyl, aryl, alkaryl or aralkyl group.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

It should be understood that the various possible stereoisomers of the compounds of Formula I are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

The term "prodrug" is used to describe refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. They generally include any pharmaceutically acceptable form (such as an ester, phosphate ester, salt of an ester or a related group) of a compound which, upon administration to a patient, provides the compound described in the specification. Nonlimiting examples are a compound which has been alkylated or acylated at an appropriate position, for example by alkylation or acylation of the secondary hydroxyl group of the probucol-like molecule.

The term "pharmaceutically acceptable derivative" refers to a derivative of the active compound that upon administration to the recipient, is capable of providing directly or indirectly, the parent compound, or that exhibits activity itself.

As used herein, the term "pharmaceutically acceptable salts" refers to salts or complexes that retain the desired biological activity of the above-identified compounds and exhibit minimal undesired toxicological effects. Nonlimiting examples of such salts are (a) acid addition salts formed with inorganic acids such as sulfate, nitrate, bicarbonate, and carbonate salts (for example, hydrochloric acid, hydrobromic acid, sulfuric acid, phosphoric acid, nitric acid, and the like), and salts formed with organic acids including tosylate, methanesulfonate, acetate, citrate, malonate, tartarate, succinate, benzoate, ascorbate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). Pharmaceutically acceptable salts may be obtained using standard procedures well known in the art, for example by reacting a sufficiently basic compound such as an amine with a suitable acid affording a physiologically acceptable anion.

Disorders

Methods and pharmaceutical compositions are provided for the treatment or prophylaxis or delay of onset of diabetes, pre-diabetes and related disorders. Related disorders of diabetes includes, but is not limited to, hyperglycemia, abnormal glucose homeostasis, insulin resistance, Syndrome X, metabolic disorders, diabetic dyslipidemia.

In one embodiment, the disease to be treated or prevented is type 2 diabetes. The chronic overabundance of glucose associated with diabetes damages the body's blood vessels and can lead to many related disorders. Generally, high glucose levels in the blood plasma (hyperglycemia) can lead higher than normal amounts of particular hemoglobin, HbA1c. Persistent or uncontrolled hyperglycemia that occurs with diabetes is associated with increased and premature morbidity and mortality. Often abnormal glucose homeostasis is associated with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, microangiopathy, kidney disorders or failure, kidney and nerve damage, cardiac disease, diabetic retinopathy and other ocular disorders, including blindness. In extreme cases, diabetes can result in the amputation of limbs and death.

Other conditions related to diabetes reported by the CDC include: nervous system diseases, which often includes impaired sensation or pain in the feet or hands, slowed digestion of food in the stomach, carpal tunnel syndrome, and other nerve problems, periodontal disease, which is a type of gum disease that can lead to tooth loss, complications of pregnancy, including congenital malformations and death of the fetus, and other complications such as diabetic ketoacidosis and hyperosmolar nonketotic coma.

Many patients who have insulin resistance or type 2 diabetes often have several symptoms that together are referred to as Syndrome X, or the metabolic syndrome. A patient having this syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670.

In one embodiment, the compound of Formula A, B, I or II, or specifically the monosuccinic acid ester of probucol is provided to a host to promote depletion of bile salts. Bile salts are steroids with detergent properties which are used to emulsify lipids in foodstuff passing through the intestine to enable fat digestion and absorption through the intestinal wall. They are secreted from the liver stored in the gall bladder and passed through the bile duct into the intestine when food is passing through. The most abundant of the bile salts in humans are cholate and deoxycholate, and they are normally conjugated with either glycine or taurine to give glycocholate or taurocholate respectively. Depletion of bile salts, including cholate and deoxycholate, force the liver to reabsorb cholesterol to make new bile.

In one embodiment, patients at risk for developing diabetes are prophylactically treated to prevent onset. Patients with diabetes or at risk for developing diabetes can be identified through several risk factors. One of the key risk factors is age and obesity. Generally patients who are 45 years or older and overweight (with a body mass index of 25 or greater) is at risk of developing diabetes.

Additional risk factors for type 2 diabetes include a family history, ethnicity (Alaska Native, American Indian, African American, Hispanic/Latino, Asian American, or Pacific Islander is at higher risk), having had gestational diabetes or giving birth to a baby weighing more than 9 pounds, previous history of high blood pressure or blood pressure of 140/90 mm Hg or higher, cholesterol levels not normal (including HDL below 35 mg/dL, or triglyceride level above 250 mg/dL), being fairly inactive (less than three times per week exercise), diagnosis of polycystic ovary syndrome, any test showing impaired glucose tolerance (IGT) or impaired fasting glucose (IFG), clinical conditions associated with insulin resistance, such as acanthosis nigricans, or a history of cardiovascular disease. Tests to be conducted can include a fasting blood glucose test or an oral glucose tolerance test.

Glucose levels of approximately 100-126 mg/dl in a fasting plasma glucose test (FPG) or approximately 140-200 mg/dl in the oral glucose tolerance test (OGTT) indicate pre-diabetes. Levels of greater than or equal to 126 mg/dl in the FPG or greater than or equal to 200 mg/dl in the OGTT indicate diabetes.

Symptoms of diabetes include increased thirst, increased hunger, fatigue, increased urination, especially at night, weight loss, blurred vision, sores that do not heal.

Pharmaceutical Compostions

Mammals, and specifically humans, suffering from diabetes or related disorder can be treated by the inhalation, systemic, oral, topical, or transdermal administration of a composition comprising an effective amount of the compounds described herein or a pharmaceutically acceptable salt, ester, pharmaceutically acceptable derivative, or prodrug thereof, optionally in a pharmaceutically acceptable carrier or diluent. The active materials can be administered by any appropriate route, for example, orally, parenterally, intravenously, intradermally, subcutaneously, or topically.

The compounds or compositions is typically administered by oral or inhalation administration. Alternatively, compounds can be administered subcutaneously, intravenously, intraperitoneally, intramuscularly, parenterally, orally, submucosally, by inhalation, transdermally via a slow release patch, or topically, in an effective dosage range to treat the target condition.

The active compound is included in the pharmaceutically acceptable carrier or diluent in an amount sufficient to deliver to a patient a therapeutically effective amount without causing serious toxic effects in the patient treated. In one embodiment, the dose of the active compound for all of the above-mentioned conditions is in the range from about 0.1 to 500 mg/kg, about 0.1 to 100 mg/kg per day, about 0.1 to 50 mg/kg per day, about 0.1 to 20 mg/kg per day, about 0.1 to 10 mg/kg per day, about 0.1 to 5 mg/kg per day, or about 0.5 to 2 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

In one embodiment, compounds of the present invention are administered orally. In one embodiment, the compounds are administered less than three times daily. In one embodiment, the compounds are administered in one or two doses daily. In one embodiment, the compounds are administered once daily. In some embodiments, the compounds are administered in a single oral dosage once a day.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch, lactose or povidone, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

In a particular embodiment, the compound is mixed with povidone.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

For systemic administration, the compound is conveniently administered in any suitable unit dosage form, including but not limited to one containing 1 to 3000 mg, 5 to 500 mg, 10 to 400 mg, 10 to 300 mg, 10 to 200 mg, 25 to 150 mg, or 10 to 100 mg of active ingredient per unit dosage form. A oral dosage of 25-350 mg is usually convenient. The unit dosage form may be administered once daily, twice daily, threes times daily or four times daily. The active ingredient should be administered to achieve peak plasma concentrations of the active compound of about 0.1 to 100 mM, preferably about 1-10 mM. This may be achieved, for example, by the intravenous injection of a solution or formulation of the active ingredient, optionally in saline, or an aqueous medium or administered as a bolus of the active ingredient.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Suitable vehicles or carriers for topical application are known, and include lotions, suspensions, ointments, creams, gels, tinctures, sprays, powders, pastes, slow-release transdermal patches, aerosols for asthma, and suppositories for application to rectal, vaginal, nasal or oral mucosa. In addition to the other materials listed herein for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

The active compounds can be prepared with carriers that protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

If administered intravenously, preferred carriers are physiological saline or phosphate buffered saline (PBS), bacteriostatic water, or Cremophor EL™ (BASF, Parsippany, N.J.).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221-229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Typical systemic dosages for all of the herein described conditions are those ranging from 0.1 mg/kg to 500 mg/kg of body weight per day as a single daily dose or divided daily doses. Preferred dosages for the described conditions range from 5-1500 mg per day. A more particularly preferred dosage for the desired conditions ranges from 10-750, 10-400, 10-300, 10-150, 20-80, or 50-100 mg per day. Typical dosages for topical application are those ranging from 0.001 to 100% by weight of the active compound. In one embodiment, the compounds are given in doses of between about 0.1-10 mg/kg. In one embodiment, the compounds are given in doses of between about 0.1-3 mg/kg. The length of dosing will range from a single dose given only once to twice daily dosages given over the course of at least six months, at least one year, or more.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Combination Therapy

The compound can also be mixed with other active materials which do not impair the desired action, or with materials that supplement the desired action. The active compounds can be administered in conjunction, i.e. combination or alternation, with other medications used in the treatment of diabetes and related disorders.

Typically used compounds include biguanides, thiazolidinediones, sulfonylureas, benzoic acid derivatives, alpha-glucosidase inhibitors, SGLT2 inhibitors and INGAP peptide. Biguanides, such as Metformin (Glucophage®), help the body use insulin more effectively. They are often used by people who are overweight, since they also help with weight control. The overall action of thiozolidinediones (TZDs) is to make cells more sensitive to insulin. Medications include Avandia® and Actos®. Rezulin® was the first thiazolidinedione, but it was withdrawn from the market after it was determined it causes liver toxicity. The other medications in this class are considered safe and effective. Sulfonylureas, such as Glucotrol® and Micronase®, are commonly prescribed medications for diabetes treatment. Sulfonylureas work by helping the body make insulin. They generally have few side effects, but cannot be used by people allergic to sulfa medications. Alpha-glucosidase inhibitors, such as Precose® and Glyset®, work by slowing down the absorption of sugar in the digestive tract. They are often used in combination with another diabetes treatment medication, such as a sulfonylurea. This type of medication can cause stomach or bowel problems in some people. Repaglinide (Prandin®) works by controlling blood sugar after meals. It is taken with meals and adjusted according to the number of meals you eat. It can be taken alone or with other medications, and has few side effects. Insulin may also be used for diabetes treatment.

Sodium glucose co-transporter 2 (SGLT2) plays a key role in maintaining glucose equilibrium in the human body, and is a molecular target to directly induce glucose excretion and to safely normalise plasma glucose in the treatment of type 2 diabetes. Chemically, most of the SGLT2 inhibitors are derived from the prototype phlorizin and structurally are glycosides, such as those in clinical studies by Sanofi-Aventis (AVE2268), GlaxoSmithKline (869682) and Bristol-Myers Squibb. Exceptions are the second generation antisense approach from ISIS Pharmaceuticals and SGLT peptide antagonists from Theratech, both in preclinical stages. Japanese companies, such as Tanabe Seiyaku with T-1095, have pioneered the SGLT inhibitor arena. SGLT2 inhibitors are also promising for other therapeutic uses such as obesity as they cause the net loss of calories from the body in form of glucose. Other examples of SGLT2 inhibitors include sergliflozin and dapagliflozin.

INGAP Peptide is a 15 amino acid sequence consisting of amino acids number 104-118 contained within the native 175 amino acid INGAP. INGAP Peptide can be synthesized through any of various means known in the art although the preferred means of synthesis is through 9-fluorenylmethoxycarbonyl (Fmoc) solid-phase synthesis. The preferred form of INGAP Peptide is the INGAP Peptide in a pharmaceutically acceptable salt form, preferably acetate salt. Formation of salts of peptides is known in the art.

INGAP Peptide has the following amino acid sequence: $NH_2$-Ile-Gly-Leu-His-Asp-Pro-Ser-His-Gly-Thr-Leu-Pro-Asn-Gly-Ser-COOH.

Examples of other active ingredients that may be administered in combination with a compound of Formula A, B, I or II, and either administered separately or in the same pharmaceutical composition, include, but are not limited to: (a) other PPAR gamma agonists and partial agonists, such as the glitazones (e.g. troglitazone, pioglitazone, englitazone, MCC-555, rosiglitazone, balaglitazone, netoglitazone, and the like), and PPAR gamma agonists and partial agonists that do not have a glitazone structure; (b) biguanides such as metformin and phenformin; (c) protein tyrosine phosphatase-1B (PTP-1B) inhibitors, (d) dipeptidyl peptidase IV (DP-IV) inhibitors; (e) insulin or insulin mimetics; (f) sulfonylureas such as tolbutamide and glipizide, or related materials; (g) α-glucosidase inhibitors (such as acarbose); (h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD4522 and other statins), (ii) bile acid sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, and (viii)

phenolic anti-oxidants, such as probucol; (i) PPARα/γ dual agonists, such as KRP-297; (j) PPARδ agonists such as those disclosed in WO97/28149; (k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists; (l) ileal bile acid transporter inhibitors; (m) agents intended for use in inflammatory conditions such as aspirin, non-steroidal anti-inflammatory drugs, glucocorticoids, azulfidine, and cyclo-oxygenase 2 selective inhibitors; (n) glucagon receptor antagonists; (o) GLP-1, GLP-1 analogs, such as exendins, GLP-1 mimetics, and GLP-1 receptor agonists; (p) GIP-1, GIP mimetics, and GIP receptor agonists; (q) PACAP, PACAP mimetics, and PACAP receptor 3 agonists.

Specific medications that can be used in combination also include: Actos® (Pioglitazone hydrochloride), Amaryl® (Glimepiride), Avandamet® (Rosiglitazone maleate with Metformin hydrochloride), Avandia® (Rosiglitazone maleate), Cozaar® (Losartan potassium), Diabinese® (Chlorpropamide), Glucophage® (Metformin hydrochloride), Glibenclamide (glyburide), Glucotrol® (Glipizide), Glucovance® (Glyburide, Metformin), Insulin, Metaglip® (Glipizide, Metformin hydrochloride), Micronase® (Glyburide), Orinase® (Tolbutamide), Prandin® (Repaglinide), Precose® (Acarbose), Starlix® (Nateglinide), Tolinase® (Tolazamide), and Xenical® (Orlistat).

Other drugs used in conjunction with the compounds of the invention that may also be useful in the treatment or amelioration of the diseases or conditions for which compounds of Formula I are useful. Such other drugs may be administered, by a route and in an amount commonly used therefore, contemporaneously or sequentially with a compound of Formula A, B, I or II. When a compound of Formula A, B, I or II is used contemporaneously with one or more other drugs, a pharmaceutical composition in unit dosage form containing such other drugs and the compound of Formula A, B, I or II is typical. However, the combination therapy also includes therapies in which the compound of Formula A, B, I or II and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula A, B, I or II.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

EXAMPLES

Figure 4:
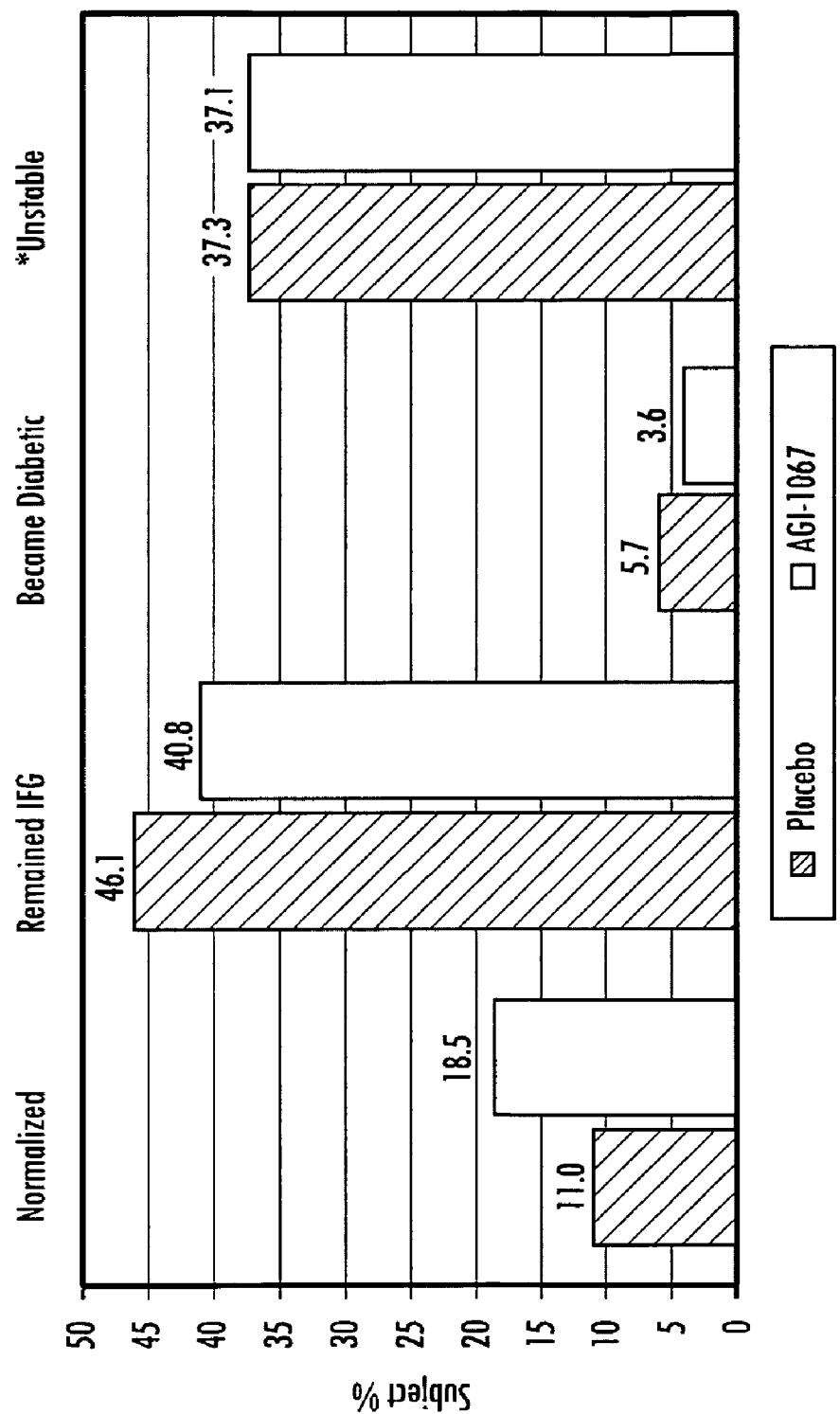
FIG. 4 shows a graph of the change in status for subjects with impaired fasting glucose at baseline.
Figure 5:
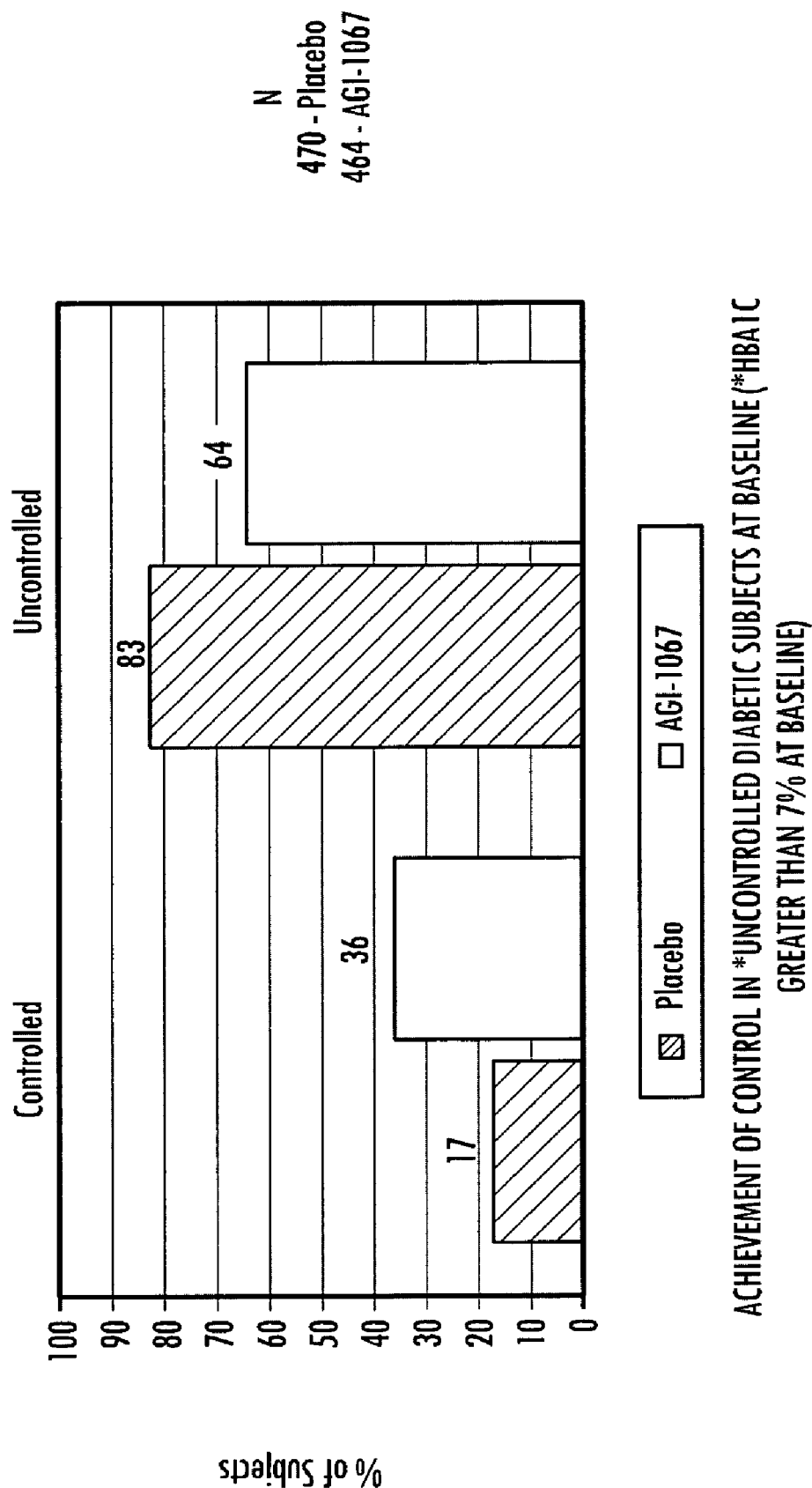
FIG. 5 shows a graph of achievement of control of subjects who were uncontrolled diabetics at baseline.
Figure 6:
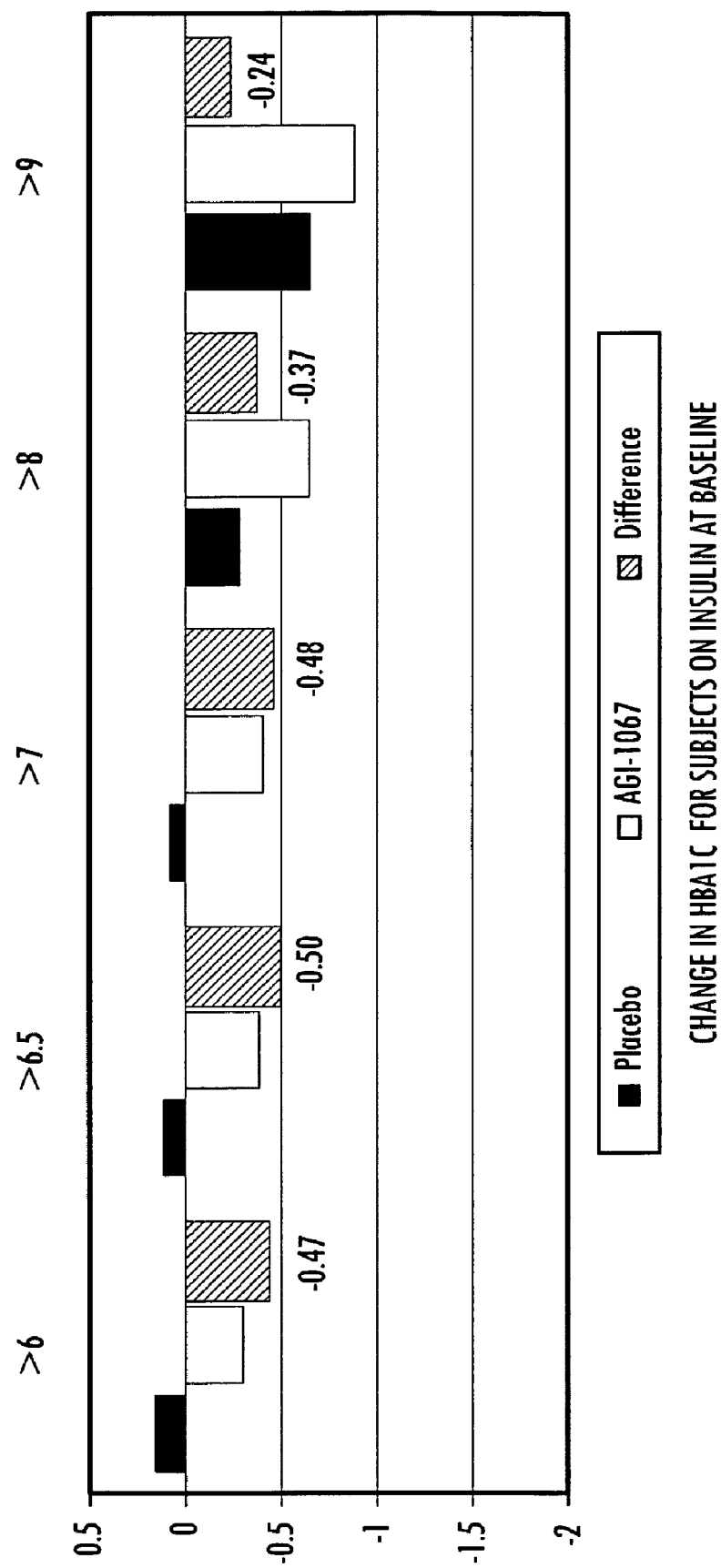
FIG. 6 shows the change in HbA1c in subjects on Insulin at baseline.
Figure 7:
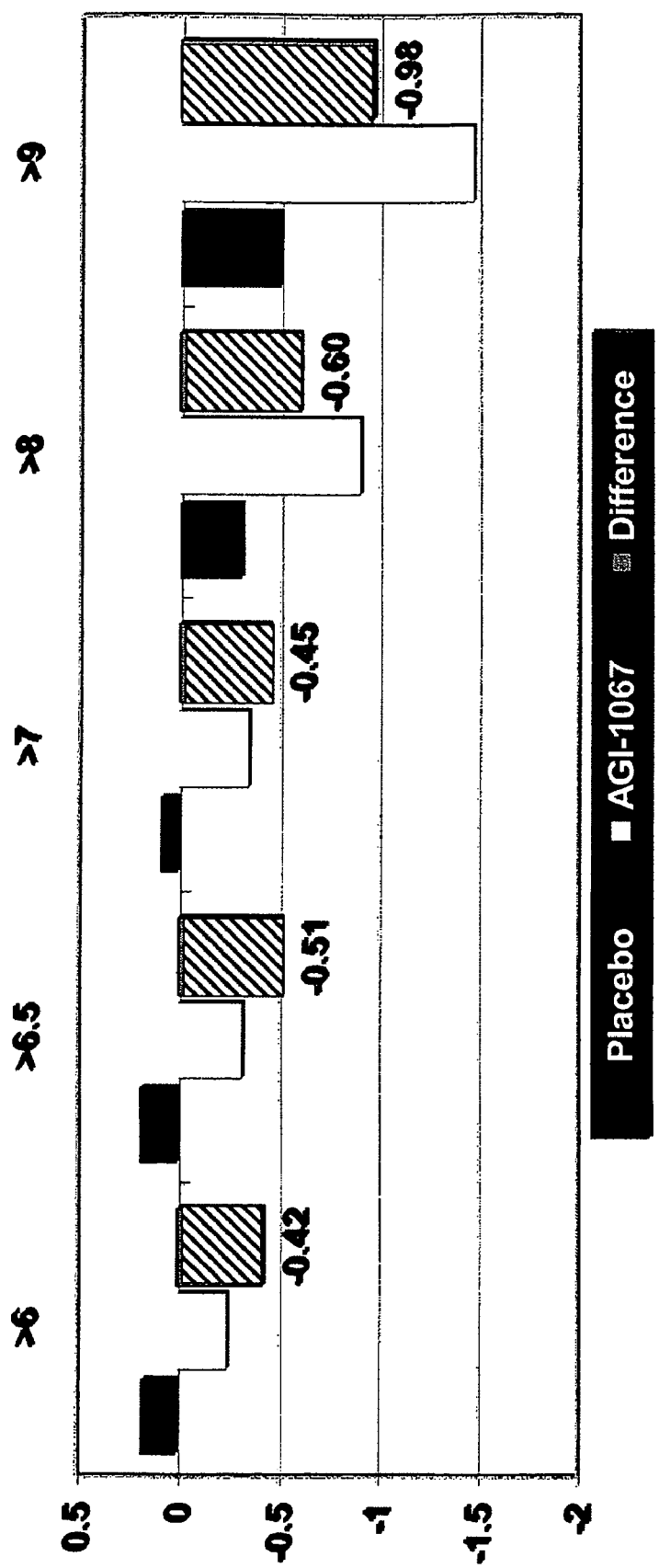
FIG. 7 shows the change in HbA1c in subjects on Pioglitazone at baseline.
Figure 8:
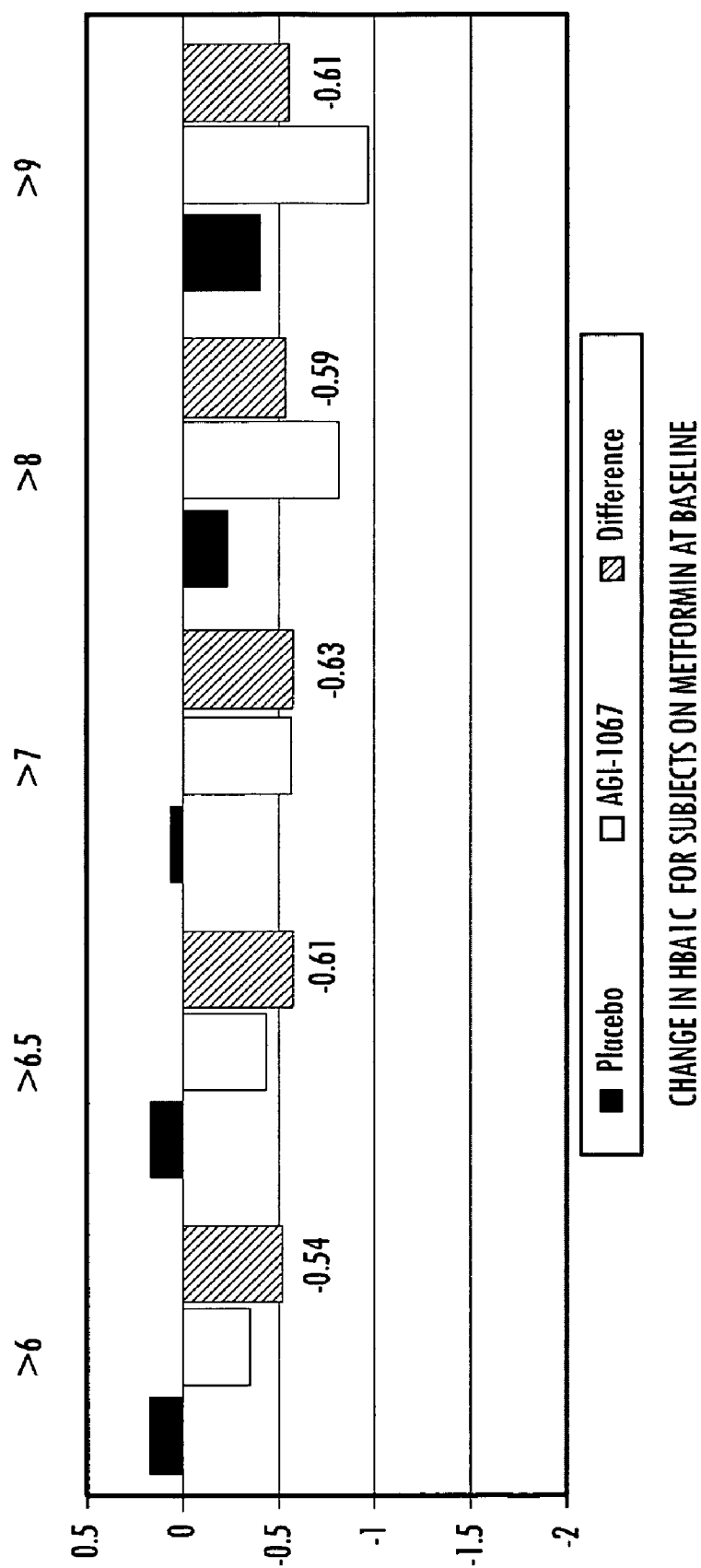
FIG. 8 shows the change in HbA1c in subjects on Metformin at baseline.
Figure 9:
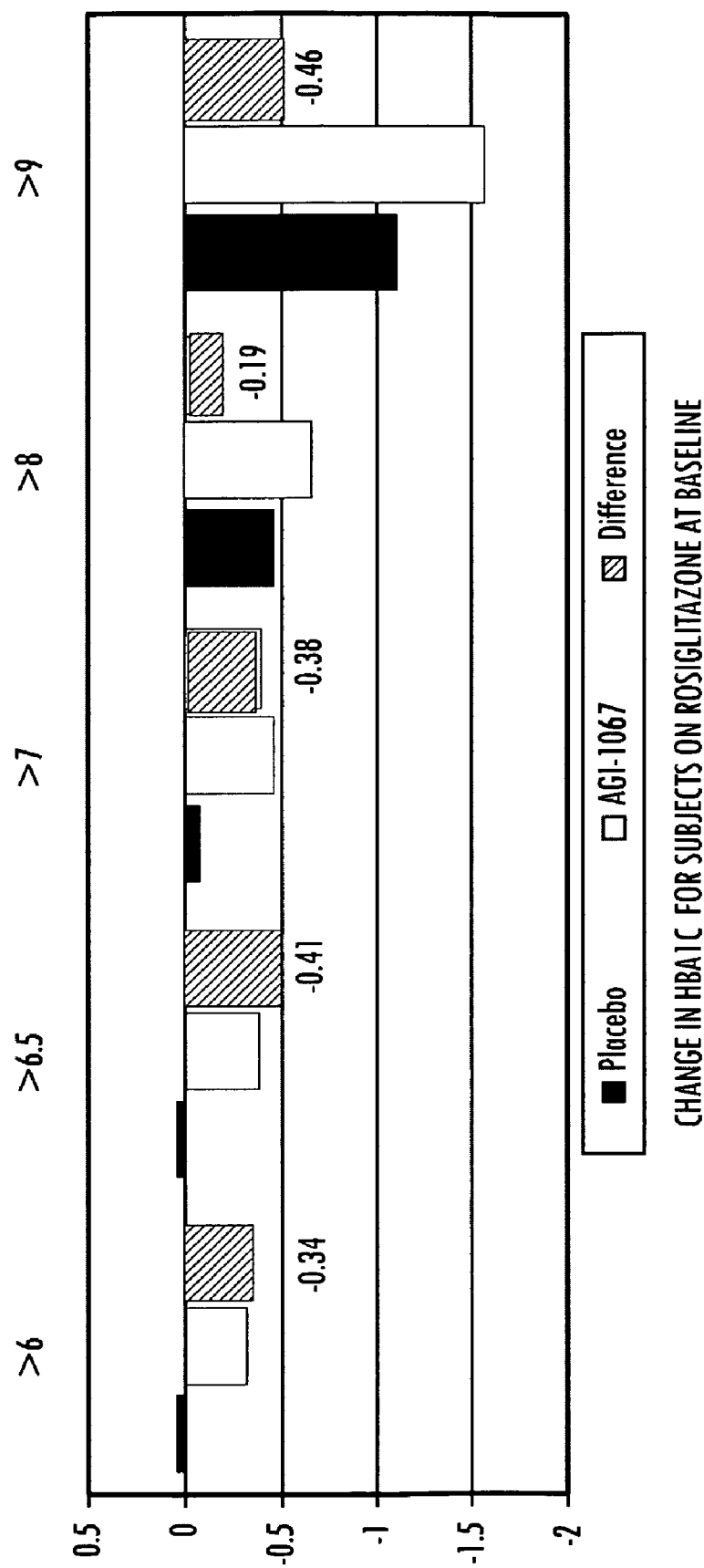
FIG. 9 shows the change in HbA1c in subjects on Rosiglitazone at baseline.
Figure 10:
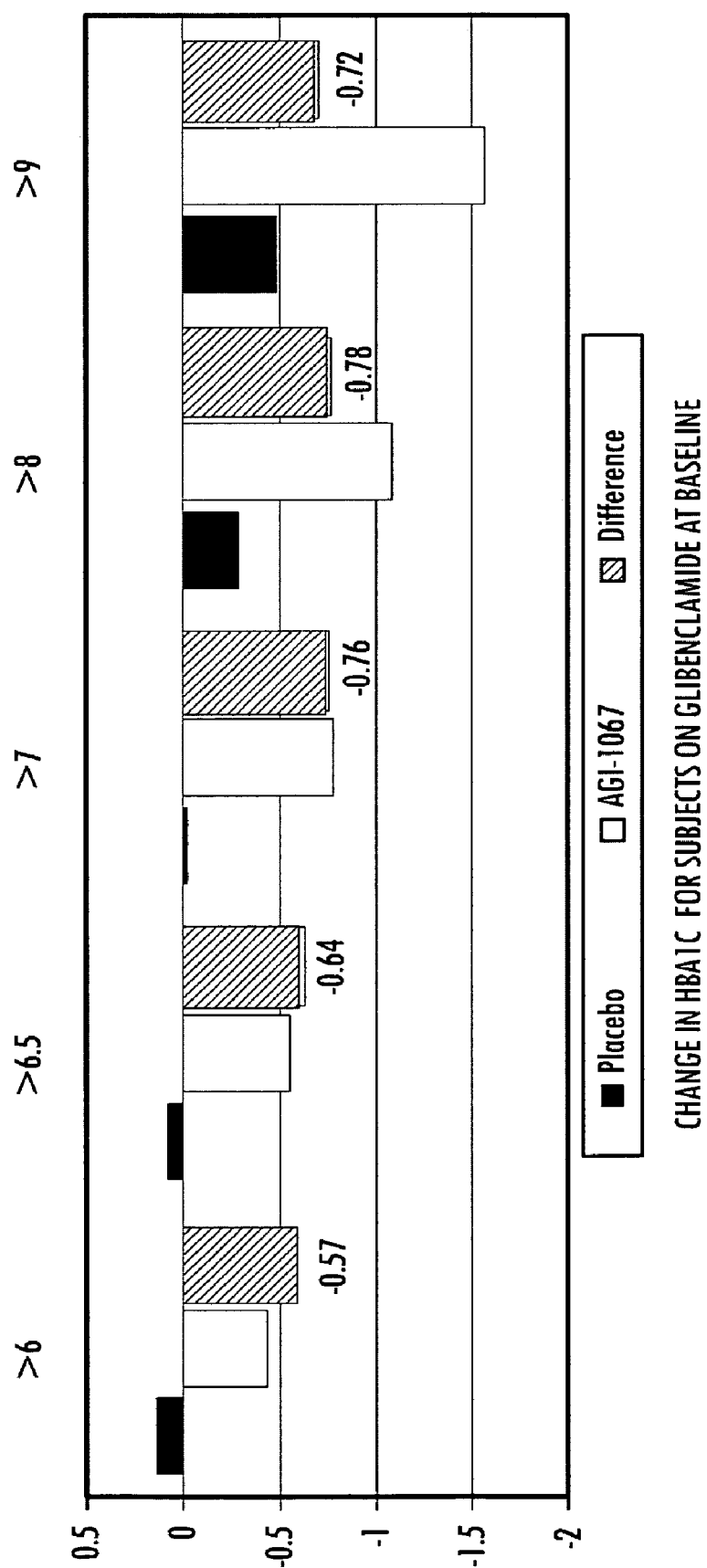
FIG. 10 shows the change in HbA1c in subjects on Glibenclamide at baseline.
Figure 11:
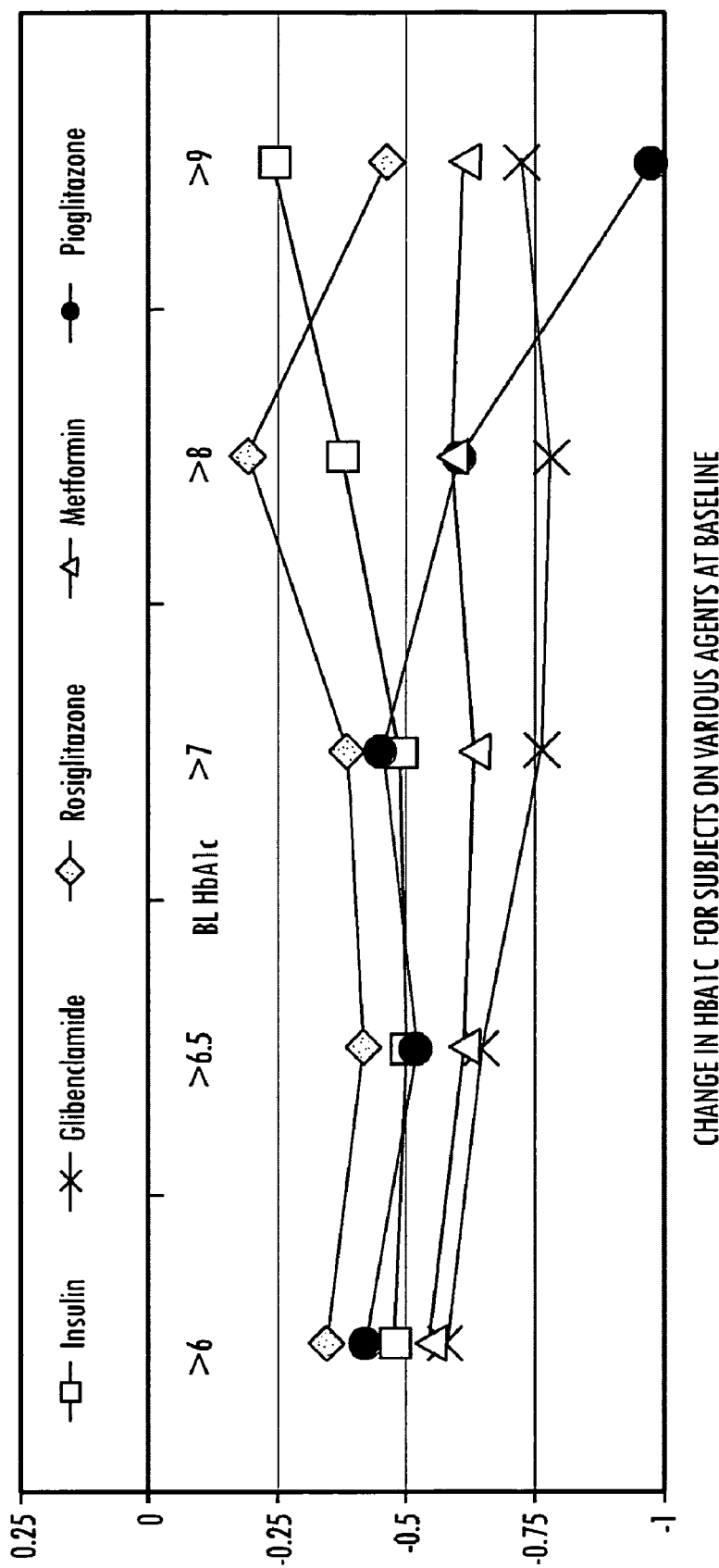
FIG. 11 shows the change in HbA1c in subjects on various agents at baseline.
Figure 12:
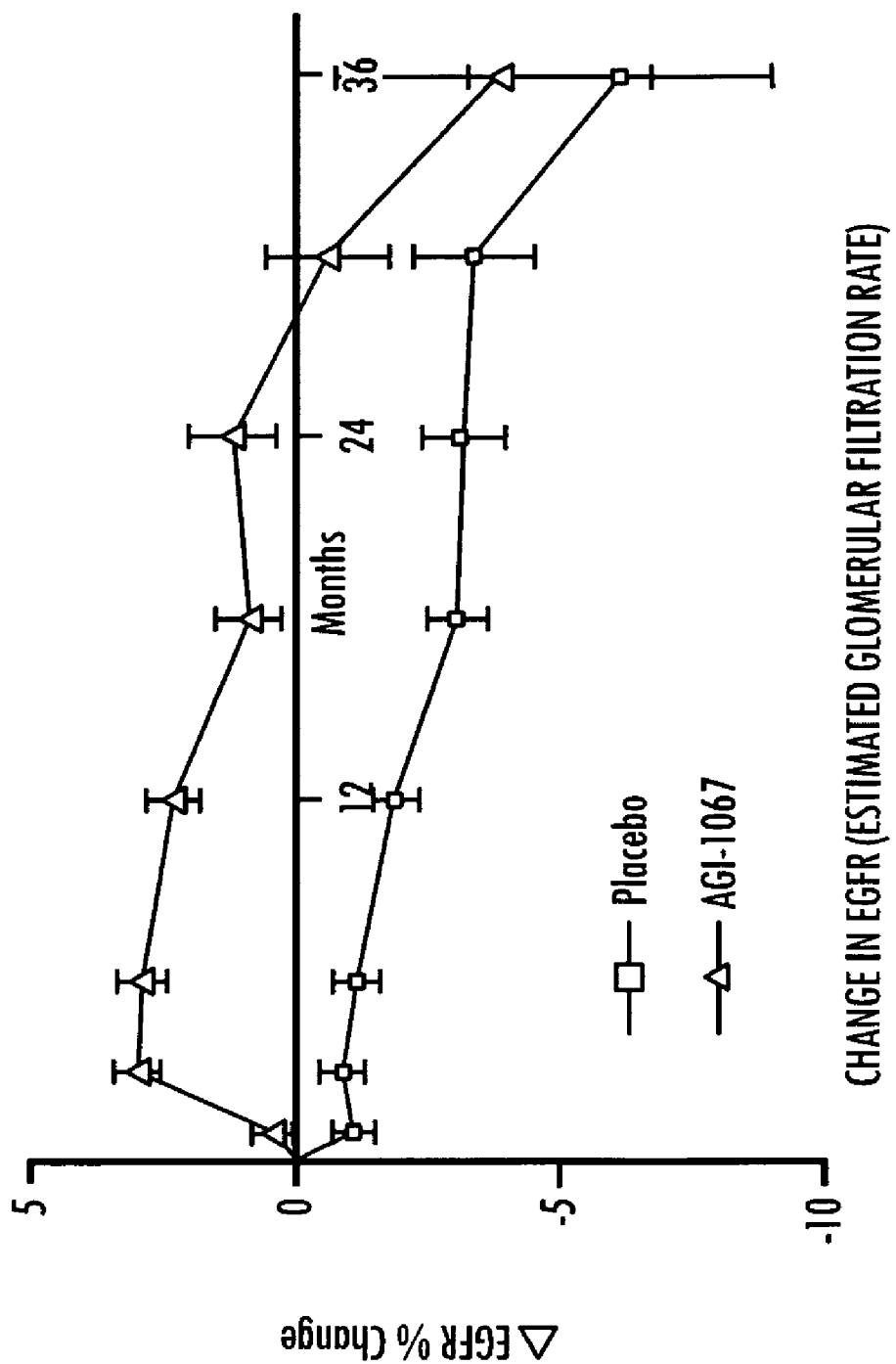
FIG. 12 shows the change in estimated glomerular filtration rate for subjects on the monosuccinic acid ester of probucol vs. placebo.
Figure 13:
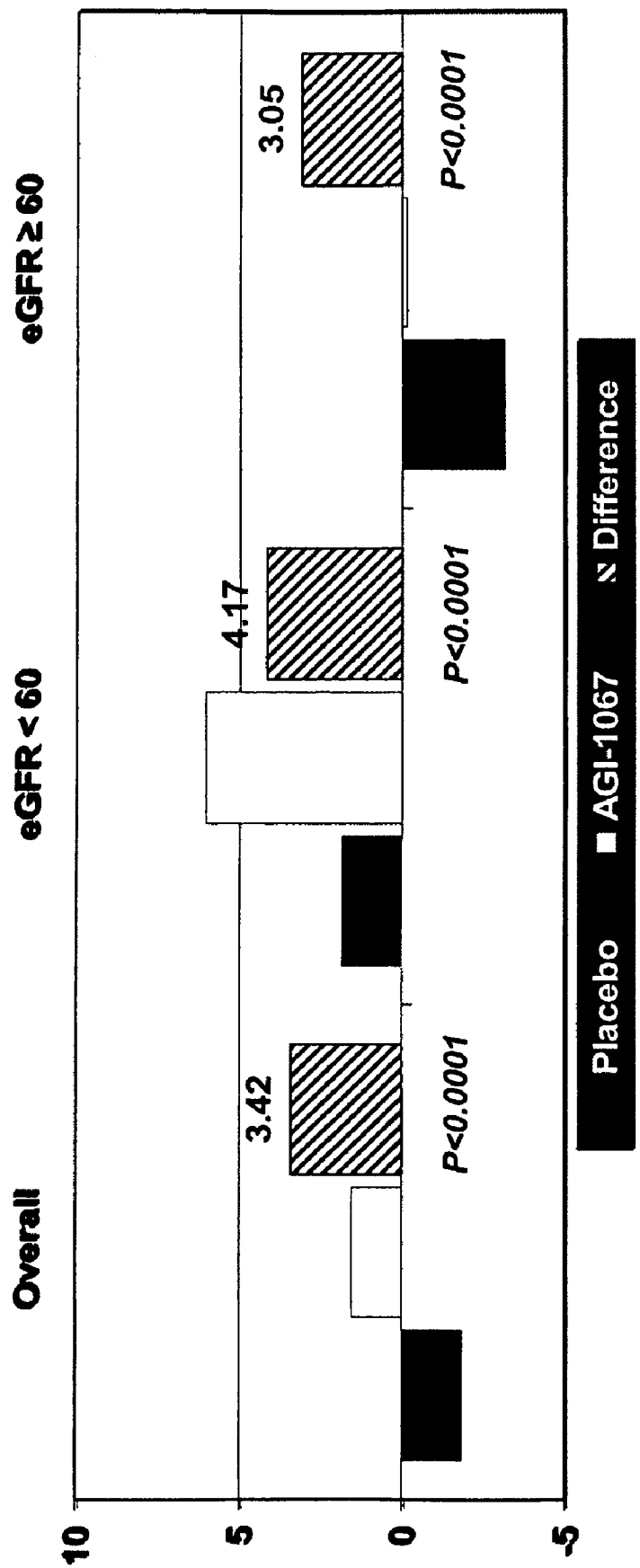
FIG. 13 shows the percent change from baseline of the eGFR.
Figure 14:
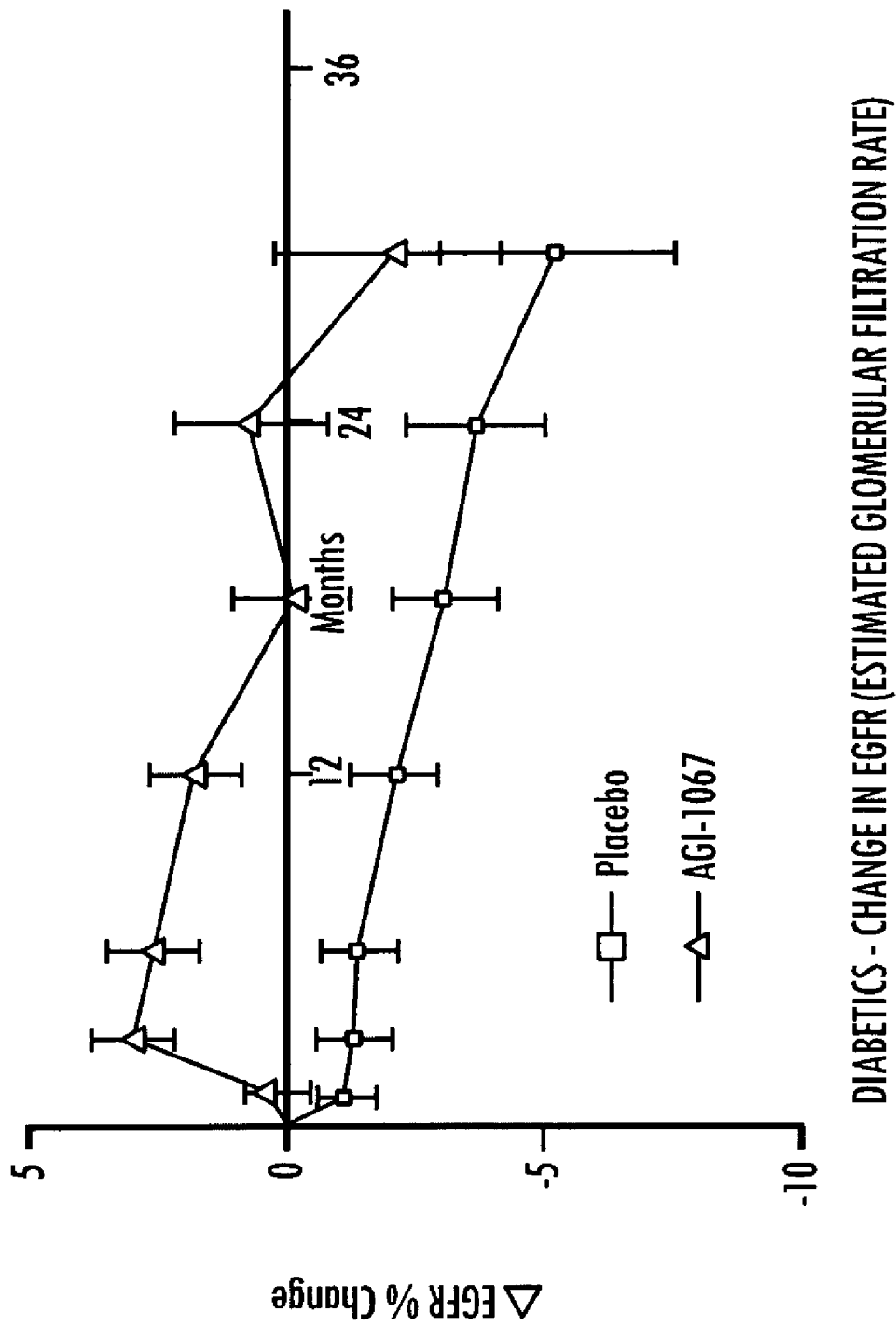
FIG. 14 is a graph of the change from baseline of the eGFR in diabetics.
Figure 16:
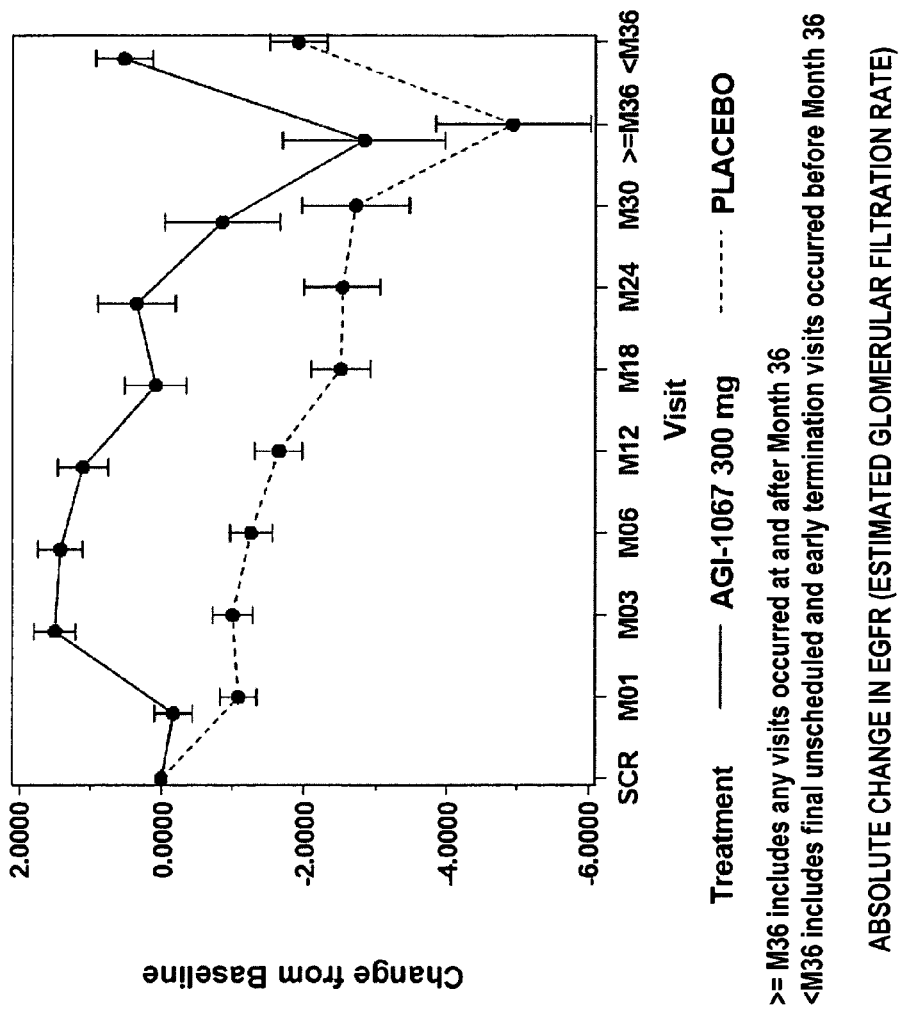
FIG. 16 is a graph of the absolute change in eGFR
Figure 18:
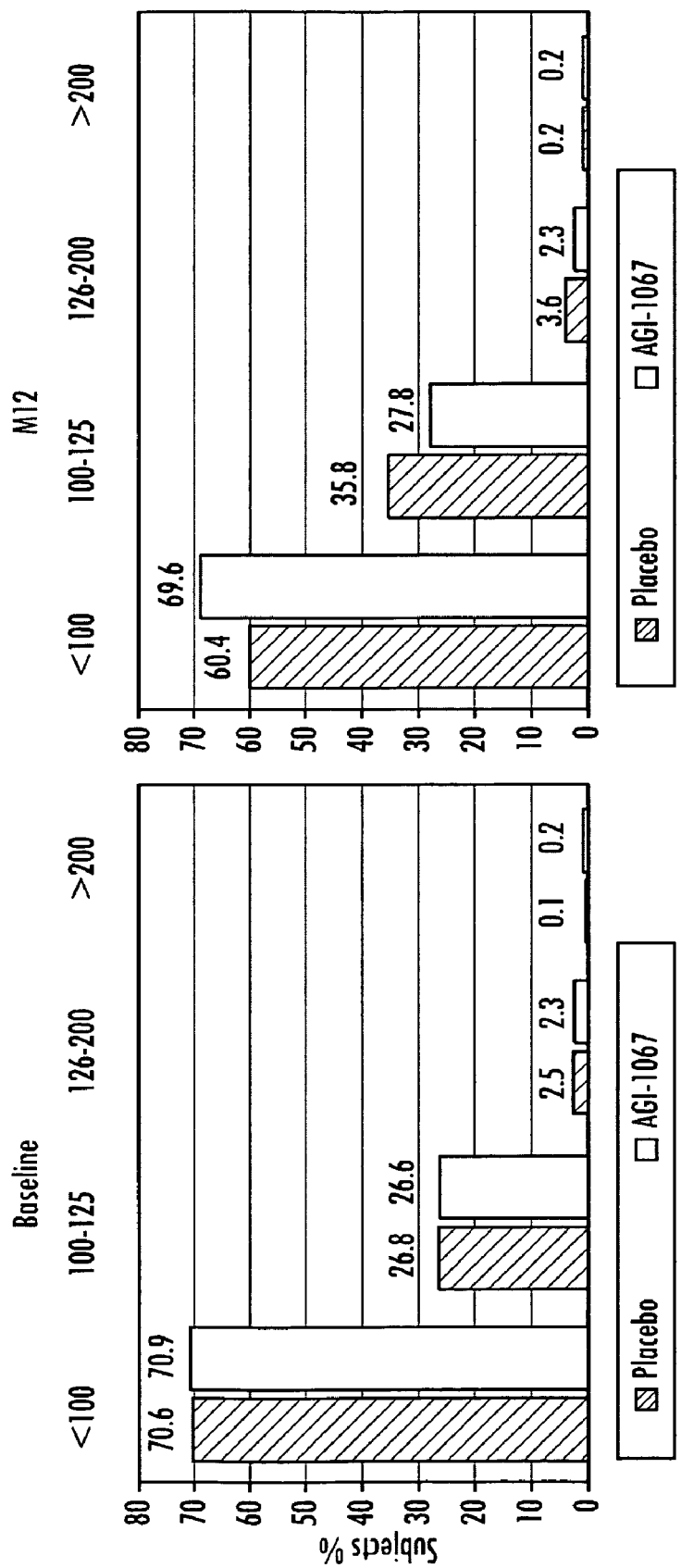
FIG. 18 is a graph showing the change in FPG for non-diabetic subjects from baseline.
Figure 19:
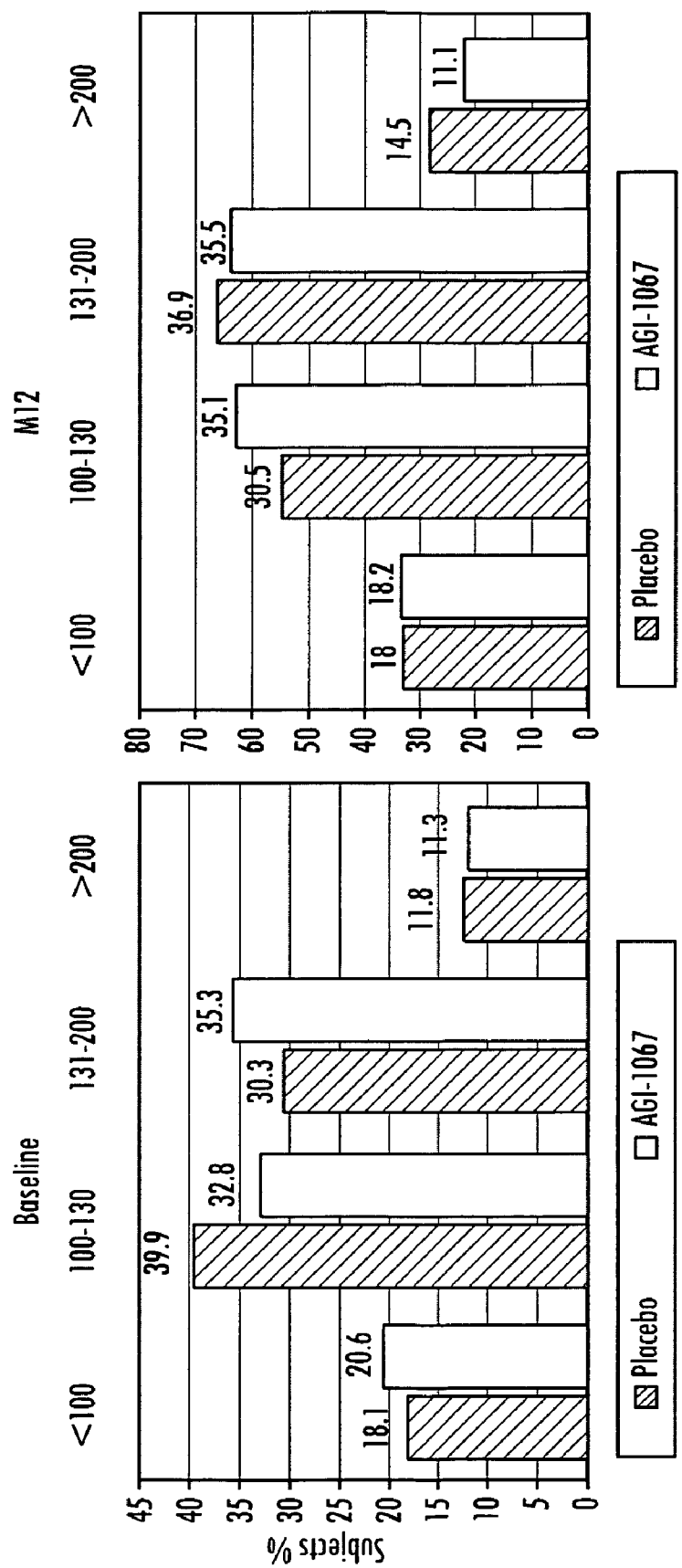
FIG. 19 is a graph showing the change in FPG for diabetic subjects from baseline.

The results shown in FIGS. 1-20 are derived from the ARISE (Aggressive Reduction of Inflammation Stops Events) trial. The ARISE trial was a Phase III, double-blind, placebo-controlled trial in over 6100 patients with a recent acute coronary syndrome (ACS). The trial was conducted in 259 cardiac centers in the United States, United Kingdom, Canada and South Africa.

The study population included 6,144 patients with previous myocardial infarction or unstable angina in a time frame >14 days and <365 days, but with no Percutaneous Coronary Intervention in last 14 days. The patients were on standard of care and kept on it for the length of the trial. Initially, all patients received a 14 day placebo "run-in" on top of standard of care and they were then split between patients receiving 300 mg/day of the monosuccinic acid ester of probucol, termed "AGI-1067" or "Succinobucol" for purposes of the study. The study lasted three years. Patients remained on standard of care regiments including: Lipid Lowering Agent (Statins, 94%; Other 17%); ACE Inhibitor or ARB, 79%; Beta-blockers, 73%; and Anti-platelet agents (Aspirin, 90%; Plavix, 57%).

Modifications and variations of the present invention will be obvious to those skilled in the art from the foregoing. All of these embodiments are considered to fall within the scope of this invention.

The invention claimed is:
1. A method for the treatment or prophylaxis of type II diabetes, a pre-diabetes condition or a diabetes related disorder in a host, comprising administering a compound of formula (B):

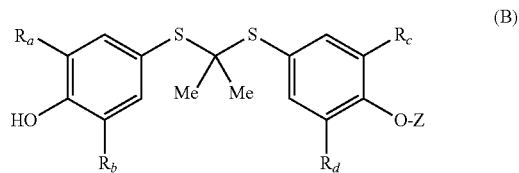

wherein
$R_a$, $R_b$, $R_c$, and $R_d$ are independently hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, $-(CH_2)_n-R_e$, $-C(O)-R_g$, and $-C(O)-(CH_2)_a-R_h$, wherein when each of $R_a$, $R_b$, $R_c$, and $R_d$ are t-butyl, Z cannot be hydrogen, and n is 1, 2, 3, 4, 5, 6, 7, 8, 9 or 10;

$R_e$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, $-CH(OH)R_k$, hydroxy, $C(O)NH_2$, C(O)NHR, $C(O)NR_2$, and epoxy;

$R_g$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, and substituted heteroaryl;

$R_h$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, $-CH(OH)R_k$, hydroxy, O-phosphate, $C(O)NH_2$, C(O)NHR, $C(O)NR_2$, C(O)-heteroaryl, C(O)-(glycine), C(O)-(arginine), C(O)-(glutamic acid), and C(O)-(lysine);

$R_k$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)R, hydroxy, C(O)NH$_2$, C(O)NHR, and C(O)NR$_2$;

R is alkyl, alkenyl, alkynyl, aryl, alkyl-C(O)OH, alkyl-C(O)O-alkyl, alkyl-C(O)O-aryl, heteroaryl, wherein any of these groups are optionally substituted, or when attached to a nitrogen atom, two adjacent R groups may combine to form a ring of 5 to 7 members; and substitutents on the groups defined above in Formula B are selected from the group consisting of alkyl, alkenyl, alkynyl, hydroxy, halo, nitro, amino, alkylamino, dialkylamino, carboxy, aryl, heteroaryl, COOR, CONH$_2$, CONHR, CONR$_2$, haloalkyl, alkoxyalkyl, mono- or polyhydroxyalkyl, CH$_2$—OR, CH$_2$—OH, OCOR, O-phosphate, SO$_2$—NH$_2$, SO$_2$—NHR, SO$_2$—NR$_2$, sulfonic acid and phosphonic acid, any of which can be further substituted wherein the diabetes related disorder is not a diabetic vascular disease, diabetic nephropathy, or a diabetic retinopathy.

2. The method of claim 1, wherein R$_a$, R$_b$, R$_c$ and R$_d$ are alkyl.

3. The method of claim 1 wherein Z is selected from the group consisting of alkyl, substituted alkyl, alkenyl, substituted alkenyl, alkynyl, substituted alkynyl, a carbohydrate group, —(CH$_2$)$_n$—R$_e$, —C(O)—R$_g$, and —C(O)—(CH$_2$)$_n$—R$_h$, and pharmaceutically acceptable salts thereof.

4. The method of claim 1 wherein Z is selected from the group consisting of alkyl, substituted alkyl, —C(O)—R$_g$, and —C(O)—(CH$_2$)$_n$—R$_h$, and pharmaceutically acceptable salts thereof.

5. The method of claim 1 wherein the host has been diagnosed with diabetes.

6. The method of claim 1 wherein the host is at risk of or diagnosed with diabetes is at risk of or diagnosed with type 2 diabetes or a pre-diabetes condition.

7. The method of claim 1 wherein the method improves insulin sensitivity in a host.

8. The method of claim 1, wherein the compound is a compound of Formula I:

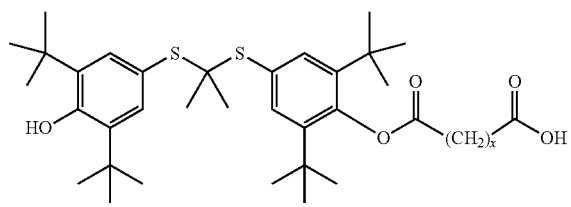

(I)

wherein x is selected from 1, 2, 3 or 4;

or a pharmaceutically acceptable salt, ester, pharmaceutically acceptable derivative, or prodrug thereof.

9. The method of claim 8 wherein x is 2 or 3.

10. The method of claim 8 wherein the host has been diagnosed with diabetes.

11. The method of claim 8 wherein the host is at risk of or diagnosed with diabetes is at risk of or diagnosed with type 2 diabetes or a pre-diabetes condition.

12. The method of claim 8 wherein the method improves insulin sensitivity in a host.

13. The method of claim 1, wherein the compound is a monosuccinic acid ester of probucol of the structure:

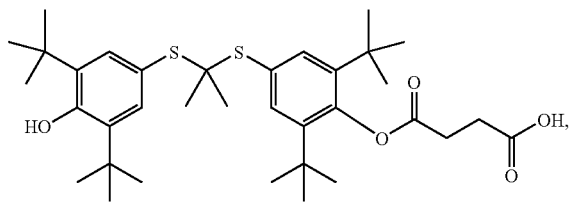

or a salt thereof.

14. The method of claim 1, wherein the compound is a compound of Formula II:

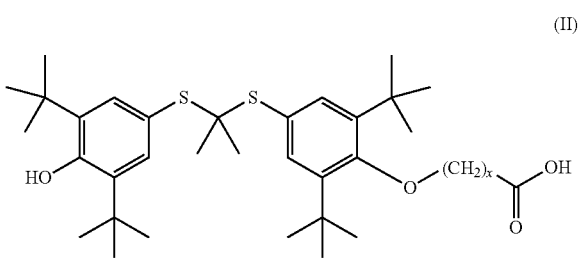

(II)

wherein x is selected from 1, 2, 3 or 4;

or a pharmaceutically acceptable salt, ester, pharmaceutically acceptable derivative, or prodrug thereof.

15. The method of claim 14 wherein x is 1.

16. The method of claim 14 wherein the host has been diagnosed with diabetes.

17. The method of claim 14 wherein the host is at risk of or diagnosed with diabetes is at risk of or diagnosed with type 2 diabetes or a pre-diabetes condition.

18. The method of claim 14 wherein the method improves insulin sensitivity in a host.

19. A method of glycemic control in a host in need thereof is provided, including administering an effective amount of a compound of Formula (B):

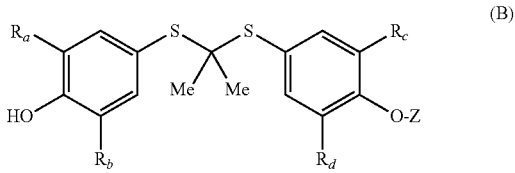

(B)

wherein

R$_a$, R$_b$, R$_c$, and R$_d$ are independently hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the R$_a$, R$_b$, R$_c$ and R$_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —(CH$_2$)$_n$—R$_e$, —C(O)—R$_g$, and —C(O)—(CH$_2$)$_n$—R$_h$, wherein when each of R$_a$, R$_b$, R$_c$, and R$_d$ are t-butyl, Z cannot be hydrogen;

n is 1, 2, 3, 4, 5, 6, 7, 8, 9 or 10;

R$_e$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH₂, NHR, NR₂, mono- or polyhydroxy-substituted alkyl, aryl, substituted aryl, heteroaryl, substituted heteroaryl, acyloxy, substituted acyloxy, COOH, COOR, —CH(OH)R$_k$, hydroxy, C(O)NH₂, C(O)NHR, C(O)NR₂, and epoxy;

R$_g$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH₂, NHR, NR₂, mono- or polyhydroxy-substituted alkyl, aryl, substituted aryl, heteroaryl, and substituted heteroaryl;

R$_h$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH₂, NHR, NR₂, mono- or polyhydroxy-substituted alkyl, aryl, substituted aryl, heteroaryl, substituted heteroaryl, acyloxy, substituted acyloxy, COOH, COOR, —CH(OH)R$_k$, hydroxy, O-phosphate, C(O)NH₂, C(O)NHR, C(O)NR₂, C(O)-heteroaryl, C(O)-(glycine), C(O)-(arginine), C(O)-(glutamic acid), and C(O)-(lysine);

R$_k$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, NH₂, NHR, NR₂, mono- or polyhydroxy-substituted alkyl, aryl, substituted aryl, heteroaryl, substituted heteroaryl, acyloxy, substituted acyloxy, COOH, COOR, —CH(OH)R, hydroxy, C(O)NH₂, C(O)NHR, and C(O)NR₂;

R is alkyl, alkenyl, alkynyl, aryl, alkyl-C(O)OH, alkyl-C(O)O-alkyl, alkyl-C(O)O-aryl, heteroaryl, wherein any of these groups are optionally substituted, or when attached to a nitrogen atom, two adjacent R groups may combine to form a ring of 5 to 7 members; and substitutents on the groups defined above in Formula B are selected from the group consisting of alkyl, alkenyl, alkynyl, hydroxy, halo, nitro, amino, alkylamino, dialkylamino, carboxy, aryl, heteroaryl, COOR, CONH₂, CONHR, CONR₂, haloalkyl, alkoxyalkyl, mono- or polyhydroxyalkyl, CH₂—OR, CH₂—OH, OCOR, O-phosphate, SO₂—NH₂, SO₂—NHR, SO₂—NR₂, sulfonic acid and phosphonic acid, any of which can be further substituted.

20. The method of claim 19, wherein R$_a$, R$_b$, R$_c$ and R$_d$ are alkyl.

21. The method of claim 19 wherein Z is selected from the group consisting of alkyl, substituted alkyl, alkenyl, substituted alkenyl, alkynyl, substituted alkynyl, a carbohydrate group, —(CH₂)$_n$—R$_e$, —C(O)—R$_g$, and —C(O)—(CH₂)$_n$—R$_h$, and pharmaceutically acceptable salts thereof.

22. The method of claim 19 wherein Z is selected from the group consisting of alkyl, substituted alkyl, —C(O)—R$_g$, and —C(O)—(CH₂)$_n$—R$_h$, and pharmaceutically acceptable salts thereof.

23. The method of claim 19, wherein the compound is a compound of Formula I:

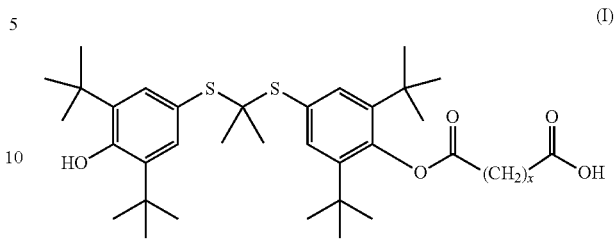

(I)

wherein x is selected from 1, 2, 3 or 4;
or a pharmaceutically acceptable salt, ester, pharmaceutically acceptable derivative, or prodrug thereof.

24. The method of claim 23 wherein x is 2 or 3.

25. The method of claim 19, wherein the compound is a monosuccinic acid ester of probucol of the structure:

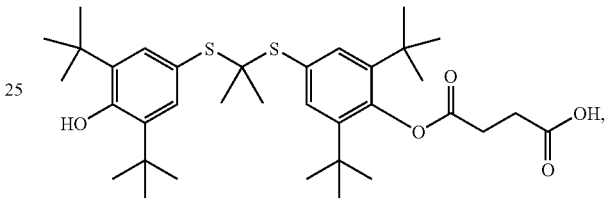

or a salt thereof.

26. The method of claim 19, wherein the compound is a compound of Formula II:

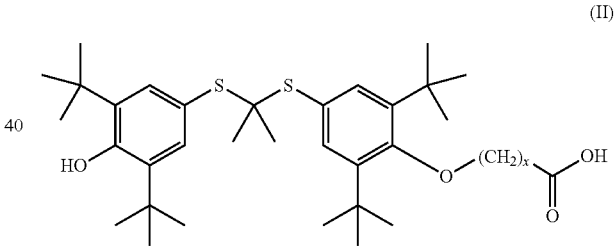

(II)

wherein x is selected from 1, 2, 3 or 4;
or a pharmaceutically acceptable salt, ester, pharmaceutically acceptable derivative, or prodrug thereof.

27. The method of claim 26 wherein x is 1.

* * * * *